United States Patent
Wang et al.

(10) Patent No.: US 11,534,759 B2
(45) Date of Patent: Dec. 27, 2022

(54) MICROFLUIDIC CHIP WITH MIXED POROSITIES FOR RESERVOIR MODELING

(71) Applicant: Saudi Arabian Oil Company, Dhahran (SA)

(72) Inventors: Wei Wang, Quincy, MA (US); Sehoon Chang, Boston, MA (US); Martin E. Poitzsch, Northumberland, NH (US)

(73) Assignee: Saudi Arabian Oil Company, Dhahran (SA)

( * ) Notice: Subject to any disclaimer, the term of this patent is extended or adjusted under 35 U.S.C. 154(b) by 149 days.

(21) Appl. No.: 17/155,619

(22) Filed: Jan. 22, 2021

(65) Prior Publication Data

US 2022/0234040 A1    Jul. 28, 2022

(51) Int. Cl.
*B01L 3/00* (2006.01)

(52) U.S. Cl.
CPC ..... *B01L 3/502715* (2013.01); *B01L 2200/10* (2013.01); *B01L 2300/0816* (2013.01)

(58) Field of Classification Search
CPC .. A61P 7/02; A61P 9/00; C12M 47/12; C12N 11/14; C12N 9/6489; C12N 7/06; C12Y 304/24087; B01L 2200/10; B01L 2300/0816; B01L 3/502715; C07K 1/12; C07K 1/14; C07K 1/16; C07K 1/18; C07K 1/34
See application file for complete search history.

(56) References Cited

U.S. PATENT DOCUMENTS

| | | | |
|---|---|---|---|
| 3,703,355 A | 11/1972 | Takahashi | |
| 3,834,122 A | 9/1974 | Allison et al. | |
| 3,851,171 A | 11/1974 | Saniford | |
| 3,947,396 A | 3/1976 | Kangas et al. | |
| 4,137,452 A | 1/1979 | Paap | |
| 4,264,329 A | 4/1981 | Beckett | |
| 4,289,203 A | 9/1981 | Swanson | |
| 4,420,565 A | 12/1983 | Schmitt | |

(Continued)

FOREIGN PATENT DOCUMENTS

| CA | 2997608 | 4/2017 |
|---|---|---|
| CA | 2941370 | 7/2018 |

(Continued)

OTHER PUBLICATIONS

Hedayat et al. "Review on fabrication techniques for porous electrodes of solid oxide fuel cells by sacrificial template methods", Renewable and Sustainable Energy Reviews, vol. 77, pp. 1221-1239, ISSN 1364-0321. (Year: 2017).*

(Continued)

*Primary Examiner* — Jennifer Wecker
*Assistant Examiner* — Jonathan Bortoli
(74) *Attorney, Agent, or Firm* — Fish & Richardson P.C.

(57) ABSTRACT

Spherical grains and sacrificial particles are mixed in a suspension. The sacrificial particles are larger than the spherical grains. The suspension is injected into a channel in a microfluidic chip, and the spherical grains form microporous structures in the channel. The microporous structures are sintered in the channel. A solvent is injected into the channel, and the solvent dissolves the sacrificial particles and forms macropores between at least some of the microporous structures, thereby forming a mixed-porosity microfluidic chip.

13 Claims, 6 Drawing Sheets

(56) References Cited

U.S. PATENT DOCUMENTS

| | | |
|---|---|---|
| 4,485,071 A | 11/1984 | Larter |
| 4,694,046 A | 9/1987 | Bock et al. |
| 4,755,469 A | 7/1988 | Showalter |
| 4,772,563 A | 9/1988 | Evangelista et al. |
| 4,882,128 A | 11/1989 | Hukvari et al. |
| 4,882,763 A | 11/1989 | Buchan et al. |
| 5,124,268 A | 6/1992 | Dakubu |
| 5,168,927 A | 12/1992 | Stegenneier |
| 5,180,556 A | 1/1993 | Nolte et al. |
| 5,390,529 A | 2/1995 | Ghiselli |
| 5,990,224 A | 11/1999 | Raynolds et al. |
| 6,226,390 B1 | 5/2001 | Deruyter et al. |
| 6,250,848 B1 | 6/2001 | Moridis et al. |
| 6,252,016 B1 | 6/2001 | Wu et al. |
| 6,331,436 B1 | 12/2001 | Richardson |
| 6,488,872 B1 | 12/2002 | Beebe et al. |
| 6,585,044 B2 | 7/2003 | Rester |
| 6,590,647 B2 | 7/2003 | Stephenson |
| 6,691,780 B2 | 2/2004 | Nguyen et al. |
| 7,032,662 B2 | 4/2006 | Malone |
| 7,033,975 B2 | 4/2006 | Baran, Jr. et al. |
| 7,249,009 B2 | 7/2007 | Ferwom et al. |
| 7,289,942 B2 | 10/2007 | Yang et al. |
| 7,303,006 B2 | 12/2007 | Stone |
| 7,373,073 B2 | 5/2008 | Kamp et al. |
| 7,472,748 B2 | 1/2009 | Gdansk et al. |
| 7,520,933 B2 | 4/2009 | Park et al. |
| 7,526,953 B2 | 5/2009 | Goodwin et al. |
| 7,588,827 B2 | 9/2009 | Nie et al. |
| 7,810,563 B2 | 10/2010 | Buijse et al. |
| 7,875,654 B2 | 1/2011 | Hong et al. |
| 7,879,625 B1 | 2/2011 | Boss |
| 7,920,970 B2 | 4/2011 | Zuo et al. |
| 8,028,562 B2 | 10/2011 | Shah et al. |
| 8,062,418 B2 | 11/2011 | Costantz et al. |
| 8,148,477 B2 | 4/2012 | Saita et al. |
| 8,176,981 B2 | 5/2012 | Savu et al. |
| 8,187,554 B2 | 5/2012 | Panagiotou |
| 8,269,501 B2 | 9/2012 | Schmidt et al. |
| 8,337,783 B2 | 12/2012 | Locascio et al. |
| 8,418,759 B2 | 4/2013 | Moore et al. |
| 8,627,902 B2 | 1/2014 | Hammer |
| 8,629,089 B2 | 1/2014 | Dams |
| 8,638,104 B2 | 1/2014 | Barber et al. |
| 8,722,812 B2 | 5/2014 | Yabu et al. |
| 8,821,806 B2 | 9/2014 | Hersherwitz et al. |
| 8,877,954 B2 | 11/2014 | Giesenberg et al. |
| 8,996,346 B2 | 3/2015 | Zuo et al. |
| 9,023,966 B2 | 5/2015 | Zhang et al. |
| 9,050,655 B2 | 6/2015 | Chou et al. |
| 9,080,097 B2 | 7/2015 | Gupta et al. |
| 9,121,271 B2 | 9/2015 | Shook |
| 9,133,709 B2 | 9/2015 | Huh et al. |
| 9,200,102 B2 | 12/2015 | Baran, Jr. et al. |
| 9,227,929 B2 | 1/2016 | Winter et al. |
| 9,279,771 B2 | 3/2016 | Aizenberg et al. |
| 9,296,851 B2 | 3/2016 | Luettgen |
| 9,366,099 B2 | 6/2016 | Ly |
| 9,375,790 B2 | 6/2016 | Murphy et al. |
| 9,481,764 B1 | 11/2016 | Kinlen et al. |
| 9,534,062 B2 | 1/2017 | He et al. |
| 9,592,555 B2 | 3/2017 | Schut et al. |
| 9,624,422 B2 | 4/2017 | Dams et al. |
| 9,664,665 B2 | 5/2017 | Gisolf et al. |
| 9,708,525 B2 | 7/2017 | Suresh et al. |
| 9,719,009 B2 | 8/2017 | Jangda et al. |
| 9,809,740 B2 | 11/2017 | Chakraborty et al. |
| 9,873,622 B2 | 1/2018 | Kang et al. |
| 9,873,827 B2 | 1/2018 | Chakraborty et al. |
| 10,273,399 B2 | 4/2019 | Cox |
| 10,308,865 B2 | 6/2019 | Cox |
| 10,308,895 B2 | 6/2019 | Vidal et al. |
| 10,316,873 B2 | 6/2019 | Weitz et al. |
| 10,392,555 B2 | 8/2019 | Giro et al. |
| 10,421,894 B2 | 9/2019 | Johnson et al. |
| 10,436,003 B2 | 10/2019 | Kim et al. |
| 10,458,207 B1 | 10/2019 | Matringe et al. |
| 10,487,259 B2 | 11/2019 | Cox |
| 10,611,967 B2 | 4/2020 | Inan |
| 10,858,931 B2 | 12/2020 | Chen et al. |
| 2001/0036667 A1 | 11/2001 | Tayebi |
| 2002/0026000 A1 | 2/2002 | Varadaraj et al. |
| 2003/0220204 A1 | 11/2003 | Baran et al. |
| 2004/0108110 A1 | 6/2004 | Zupanick et al. |
| 2004/0143059 A1 | 7/2004 | Cabrera et al. |
| 2005/0080209 A1 | 4/2005 | Blankenship et al. |
| 2005/0252286 A1 | 11/2005 | Ibrahim et al. |
| 2006/0088476 A1 | 4/2006 | Harder |
| 2006/0105052 A1 | 5/2006 | Acar et al. |
| 2006/0120683 A1 | 6/2006 | Kamp et al. |
| 2007/0114030 A1 | 5/2007 | Todd et al. |
| 2007/0119244 A1 | 5/2007 | Goodwin et al. |
| 2008/0019921 A1 | 1/2008 | Zhang |
| 2008/0110253 A1 | 5/2008 | Stephenson et al. |
| 2008/0111064 A1 | 5/2008 | Andrews et al. |
| 2008/0206317 A1 | 8/2008 | Johnsson et al. |
| 2008/0220970 A1 | 9/2008 | Martin |
| 2009/0087911 A1 | 4/2009 | Rogerio |
| 2009/0087912 A1 | 4/2009 | Ramos et al. |
| 2009/0173253 A1 | 7/2009 | Roesch et al. |
| 2009/0174117 A1 | 7/2009 | Winkler et al. |
| 2009/0248309 A1 | 10/2009 | Nelville et al. |
| 2009/0253595 A1 | 10/2009 | Qu et al. |
| 2009/0277625 A1 | 11/2009 | Bai et al. |
| 2010/0049625 A1 | 2/2010 | Biebesheimer et al. |
| 2010/0068821 A1 | 3/2010 | St Germain |
| 2010/0092865 A1 | 4/2010 | Kanno et al. |
| 2010/0224823 A1 | 9/2010 | Yin et al. |
| 2010/0233009 A2* | 9/2010 | Neirinek ............... C25D 13/02 419/2 |
| 2010/0270020 A1 | 10/2010 | Baran et al. |
| 2010/0290999 A1 | 11/2010 | Kim |
| 2010/0305219 A1 | 12/2010 | Granick et al. |
| 2010/0307745 A1 | 12/2010 | Lafitte |
| 2011/0012331 A1 | 1/2011 | Kim |
| 2011/0030949 A1 | 2/2011 | Weaver et al. |
| 2011/0129424 A1 | 6/2011 | Berkland et al. |
| 2011/0207231 A1 | 8/2011 | Natan et al. |
| 2011/0239754 A1 | 10/2011 | Dyer |
| 2011/0260051 A1 | 10/2011 | Preudhomme et al. |
| 2011/0275061 A1 | 11/2011 | Weidemaier et al. |
| 2011/0320128 A1 | 12/2011 | Shook |
| 2012/0062886 A1 | 3/2012 | Piotti |
| 2012/0115128 A1 | 5/2012 | Miller |
| 2012/0135080 A1 | 5/2012 | Bromberg et al. |
| 2012/0175120 A1 | 7/2012 | Holcomb et al. |
| 2012/0193578 A1 | 8/2012 | Pan et al. |
| 2012/0257199 A1 | 10/2012 | Liu et al. |
| 2012/0261617 A1 | 10/2012 | Pan et al. |
| 2012/0325465 A1 | 12/2012 | Hammer et al. |
| 2013/0040292 A1 | 2/2013 | Lopez et al. |
| 2013/0084630 A1 | 4/2013 | Rolland et al. |
| 2013/0084643 A1 | 4/2013 | Commarieu et al. |
| 2013/0087020 A1 | 4/2013 | Brutchey et al. |
| 2013/0087329 A1 | 4/2013 | Hewitt |
| 2013/0087340 A1 | 4/2013 | Choens et al. |
| 2013/0109261 A1 | 5/2013 | Koene |
| 2013/0126158 A1 | 5/2013 | Gupta |
| 2013/0172853 A1 | 7/2013 | McClain |
| 2013/0244914 A1 | 9/2013 | Wu et al. |
| 2013/0259808 A1 | 10/2013 | Chen et al. |
| 2013/0296453 A1 | 11/2013 | Giesenberg et al. |
| 2013/0312970 A1 | 11/2013 | Lafitte et al. |
| 2013/0341030 A1 | 12/2013 | Brannon et al. |
| 2014/0060832 A1 | 3/2014 | Mahoney et al. |
| 2014/0077121 A1 | 3/2014 | Sun et al. |
| 2014/0122047 A1 | 5/2014 | Saldivar et al. |
| 2014/0186939 A1 | 7/2014 | Peterman et al. |
| 2014/0190700 A1 | 7/2014 | Tang et al. |
| 2014/0208825 A1 | 7/2014 | Holba et al. |
| 2014/0231077 A1 | 8/2014 | Rivero et al. |
| 2014/0260694 A1 | 9/2014 | Szlendak |
| 2014/0323363 A1 | 10/2014 | Perriat |
| 2014/0360973 A1 | 12/2014 | Yin et al. |

(56) References Cited

U.S. PATENT DOCUMENTS

| | | |
|---|---|---|
| 2015/0001385 A1 | 1/2015 | Perriat et al. |
| 2015/0013983 A1 | 1/2015 | Alwattari |
| 2015/0038347 A1 | 2/2015 | Johnson et al. |
| 2015/0050741 A1 | 2/2015 | Tour et al. |
| 2015/0079270 A1 | 3/2015 | Wang et al. |
| 2015/0118501 A1 | 4/2015 | Lu |
| 2015/0132543 A1 | 5/2015 | Nouzille et al. |
| 2015/0132742 A1 | 5/2015 | Thou et al. |
| 2015/0148269 A1 | 5/2015 | Tamsilian |
| 2015/0153472 A1 | 6/2015 | Tour |
| 2015/0159079 A1 | 6/2015 | Huh et al. |
| 2015/0175876 A1 | 6/2015 | Resasco et al. |
| 2015/0232748 A1 | 8/2015 | Kanj et al. |
| 2015/0268370 A1 | 9/2015 | Johnston et al. |
| 2015/0299369 A1 | 10/2015 | Ausserre et al. |
| 2015/0368547 A1 | 12/2015 | Lesko et al. |
| 2015/0376493 A1 | 12/2015 | Huh et al. |
| 2016/0003040 A1 | 1/2016 | Jessheim et al. |
| 2016/0016166 A1 | 1/2016 | Rolland et al. |
| 2016/0040514 A1 | 2/2016 | Rahmani et al. |
| 2016/0061020 A1 | 3/2016 | Sayarpour |
| 2016/0061790 A1 | 3/2016 | Zhang |
| 2016/0075937 A1 | 3/2016 | Cannan |
| 2016/0083641 A1 | 3/2016 | Gamage |
| 2016/0097750 A1 | 4/2016 | Van Herzen |
| 2016/0129371 A1 | 5/2016 | Black |
| 2016/0251571 A1 | 9/2016 | Agrawal et al. |
| 2016/0264846 A1 | 9/2016 | Bennetzen et al. |
| 2016/0340569 A1 | 11/2016 | Belcher |
| 2017/0059668 A1 | 3/2017 | Chang et al. |
| 2017/0067322 A1 | 3/2017 | Wong |
| 2017/0173546 A1 | 6/2017 | Cheng et al. |
| 2017/0199124 A1 | 7/2017 | Bolduc et al. |
| 2018/0275114 A1 | 9/2018 | Kosynkin |
| 2018/0369808 A1 | 12/2018 | Wronko |
| 2019/0016943 A1 | 1/2019 | Ren et al. |
| 2019/0118175 A1 | 4/2019 | Kim et al. |
| 2019/0218907 A1 | 7/2019 | Ow et al. |
| 2019/0226326 A1 | 7/2019 | Ow et al. |
| 2019/0368336 A1 | 12/2019 | Hammond et al. |
| 2020/0116019 A1 | 4/2020 | Ow et al. |
| 2020/0377626 A1 | 12/2020 | Ow et al. |
| 2020/0408089 A1 | 12/2020 | Ow et al. |

FOREIGN PATENT DOCUMENTS

| | | |
|---|---|---|
| CA | 2916567 | 8/2019 |
| CN | 101475667 | 7/2009 |
| CN | 102649831 | 8/2012 |
| CN | 103160265 | 6/2013 |
| CN | 103267825 | 8/2013 |
| CN | 103275270 | 9/2013 |
| CN | 103352255 | 10/2013 |
| CN | 103508411 | 1/2014 |
| CN | 102586873 | 12/2014 |
| CN | 104616350 | 5/2015 |
| CN | 107915802 | 4/2018 |
| EP | 0171978 | 11/1990 |
| EP | 1721603 | 11/2006 |
| EP | 2004573 | 12/2008 |
| EP | 2040075 | 3/2009 |
| EP | 2104082 | 9/2009 |
| EP | 1404776 | 11/2012 |
| EP | 2480625 | 4/2013 |
| EP | 2480626 | 4/2013 |
| EP | 3444028 | 2/2019 |
| FR | 2756046 | 5/1998 |
| FR | 2928484 | 9/2009 |
| GB | 2161269 | 8/1988 |
| GB | 2489714 | 10/2012 |
| KR | 20170131731 | 11/2017 |
| KR | 101852925 | 4/2018 |
| WO | WO 1999038931 | 8/1999 |
| WO | WO 2002102917 | 12/2002 |
| WO | WO 2003100214 | 12/2003 |
| WO | WO 2004095259 | 11/2004 |
| WO | WO 2007124814 | 11/2007 |
| WO | WO 2008034553 | 3/2008 |
| WO | WO 2010138914 | 12/2010 |
| WO | WO 2011035294 | 3/2011 |
| WO | WO 2011063023 | 5/2011 |
| WO | WO 2011081681 | 7/2011 |
| WO | WO 2011035292 | 10/2011 |
| WO | WO 2012052148 | 4/2012 |
| WO | WO 2012154332 | 11/2012 |
| WO | WO 2012158478 | 11/2012 |
| WO | WO 2013142869 | 9/2013 |
| WO | WO 2014008496 | 1/2014 |
| WO | WO 2014014919 | 1/2014 |
| WO | WO 2014066793 | 5/2014 |
| WO | WO 2014179020 | 11/2014 |
| WO | WO 2014207075 | 12/2014 |
| WO | WO 2015044446 | 4/2015 |
| WO | WO 2015058206 | 4/2015 |
| WO | WO 2015097116 | 7/2015 |
| WO | WO 2015200060 | 12/2015 |
| WO | WO 2016087397 | 6/2016 |
| WO | WO 2016174413 | 11/2016 |
| WO | WO 2017015120 | 1/2017 |
| WO | WO 2017136641 | 8/2017 |
| WO | WO 2017164822 | 9/2017 |
| WO | WO 2017210424 | 12/2017 |
| WO | WO 2018085504 | 5/2018 |
| WO | WO 2018175763 | 9/2018 |
| WO | WO 2018234431 | 12/2018 |
| WO | WO 2019027817 | 2/2019 |
| WO | WO 2019063100 | 4/2019 |

OTHER PUBLICATIONS

Rouquerol, et al. Recommendations for the Characterization of Porous Solids. Pure and Applied Chemistry. 66. 1739-. 10.1351/pac199466081739. (Year: 1994).*

Agenet et al., "Fluorescent Nanobeads: a First Step Toward Intelligent Water Tracers," SPE-157019, Society of Petroleum Engineers (SPE), presented at the SPE International Oilfield Nanotechnology Conference held in Noordwijk, the Netherlands, Jun. 12-14, 2012, 13 pages.

Alfazazi et al., "Screening of New HPAM Base Polymers for Applications in High Temperature and High Salinity Carbonate Reservoirs," SPE-192805-MS, Society of Petroleum Engineers (SPE), presented at Abu Dhabi International Petroleum Exhibition & Conference, Nov. 12-15, 2018, 17 pages.

Allard and Larpent, "Core-shell type dually fluorescent polymer nanoparticles for ratiometric pH-sensing," J. Polym. Sci., Part A: Polym. Chem. 46:18 (6206-6213), 2008, 8 pages.

Al-Muntasheri et al., "Nanoparticle-Enhanced Hydraulic-Fracturing Fluids: A Review," SPE185161-PA, Society of Petroleum Engineers (SPE), SPE Production & Operations 32:02, May 2017, 10 pages.

Anbari et al., "Microfluidic Model Porous Media: Fabrication and Applications," Nano Micro Small, Special Issue: Multi-Scale Pores and Channels, May 3, 2018, 14:18 (1703575), 15 pages.

Anisimov, "The Use of Tracers for Reservoir Characterization," SPE 118862, Society of Petroleum Engineers (SPE), presented at SPE Middle East Oil and Gas Show and Conference, Mar. 15-18, 2009, 8 pages.

Annen et al., "A facile synthesis of dispersible NaCl nanocrystals," Dalton Transactions, Nov. 2009, 44: 9731-9734, 5 pages.

Armelao et al., "Design of luminescent lanthanide complexes: From molecules to highly efficient photo-emitting materials," Coordination Chemistiy Reviews, 254: 487-505, Mar. 2010, 19 pages.

Armstrong et al., "Artificial opal photonic crystals and inverse opal structures—fundamentals and applications from optics to energy storage," Journal of Materials Chemistry C, May 2015, 3: 6109-6143, 35 pages.

Asadi et al., "Application of Chemical Tracers in IOR: A Case History," SPE-126029-MS, Society of Petroleum Engineers (SPE), presented at the SPE North African Technical Conference and Exhibition, Feb. 14-17, 2010, 11 pages.

(56) References Cited

OTHER PUBLICATIONS

Asano et al., "Development of paper-based microfluidic analytical device for iron assay using photomask printed with 3D printer for fabrication of hydrophilic and hydrophobic zones on paper by photolithography," Analytica Chimica Acta, 883:55-60, Apr. 9, 2015, 6 pages.

Aslan et al., "Fluorescent Core—Shell AG@$SiO_2$ Nanocomposites for Metal-Enhanced Fluorescence and Single Nanoparticle Sensing Platforms," JACS Communications, J. Am. Chem. Soc. 129: 1524-1525, Jan. 19, 2007, 2 pages.

Atarita et al., "Predicting Distribution of Total Organic Carbon (TOC) and S2 with Δ Log Resistivity and Acoustic Impedance Inversion on Talang Akar Formation, Cipunegara Sub Basin, West Java," Procedia Engineering, 2017, 170: 390-397, 8 pages.

Badgett et al., "Totalsynthese eines Neobetanidin-Derivates und des Neobetenamins," Helvetica Chimica Acta 53(2): 433-448, 1970, 16 pages, English Summary.

Bagaria et al., "Iron Oxide Nanoparticles Grafted with Sulfonated Copolymers are Stable in Concentrated Brine at Elevated Temperatures and Weakly Adsorb on Silica," ACS Applied Materials & Interfaces, 5:8 (3329-3339), Mar. 25, 2013, 11 pages.

Bala et al., "Interaction of Different Metal Ions with Carboxylic Acid Group: A Quantitative Study," The Journal of Physical Chemistiy A, 111:28 (6183-6190), Jun. 2007, 8 pages.

Bao et al., "Luminescence properties of the co-luminescence groups of Sm—La-pyridyl carboxylic acids," Journal of Rare Earths 30:4 (320-324), Apr. 2012, 5 pages.

Behnke et al., "Encapsulation of Hydrophobic Dyes in Polystyrene Micro- and Nanoparticles via Swelling Procedures." J. Fluoresc. 21(3): 937-944, 2011, 8 pages.

Benninger et al., "Time-resolved fluorescence imaging of solvent interaction in microfluidic devices," Optics Express, Sep. 2005, 11 pages.

Blanz et al., "Nuclear Magnetic Resonance Logging While Drilling (NMR-LWD): From an Experiment to a Day-to-Day Service for the Oil Industry," Diffusion Fundamentals, 2010, 14(2), 5 pages.

Borrini et al., "Water Soluble PDCA Derivatives for Selective Ln(III)/An(III) and Am(III)/Cm(III) Separation," Solvent Extraction and Ion Exchange 33:3 (224-235), Oct. 2014, 30 pages.

Boyjoo et al., "Synthesis of micro and nano-sized calcium carbonate particles and their applications," Journal of Materials Chemistiy A, 2014, 2: 14270-14288, 19 pages.

Brichart et al., "The Use of Fluorescent Tracers for Inhibitor Concentration Monitoring Useful for Scale Inhibitor," IPTC-17933-MS, International Petroleum Technology Conference, presented at the International Petroleum Technology Conference held in Kuala Lumpur, Dec. 10-12, 2014, 8 pages.

Buchgraber et al., "Creation of a dual-porosity micromodel for pore-level visualization of multiphase flow," J. Petrol, Sci. Eng., 2012, 86-87: 27-38, 12 pages.

Bunzli and Piguet, "Taking advantage of luminescent lanthanide ions," Chemical Society Reviews, 34:12 (1048-1077), Sep. 2005, 30 pages.

Chang et al., "Magnetic SERS Composite Nanoparticles for Microfluidic Detection," 251st ACS National Meeting, Mar. 13-17, 2016, 1 pages, abstract only.

Chen et al., "Aggregation Kinetics of Alginate-Coated Hematite Nanoparticles in Monovalent and Divalent Electrolytes," Environmental Science & Technology, 40:5 (1516-1523), Mar. 2006, 8 pages.

Chen et al., "Analysis of the solution conformations of T4 lysozyme by paramagnetic NMR spectroscopy," The Royal Society of Chemistry, Physical Chemistry Chemical Physics (PCCP) 18:8 (5850-5859), 2016, 10 pages.

Chen et al., "Hydration Repulsion between Carbohydrate Surfaces Mediated by Temperature and Specific Ions," Scientific Reports, vol. 6 (1-10), Jun. 23, 2016, 10 pages.

Chen et al., "Impact of Irreversible Retention on Tracer Deployments; Constraining Novel Material Deployments," SPE 188890-MS, Society of Petroleum Engineers (SPE), presented at the SPE Abu Dhabi International Petroleum Exhibition and Conference, Nov. 2017, 8 pages.

Chen et al., "Improved Reservoir History Matching and Production Optimization with Tracer Data," SPE 191523-MS, Society of Petroleum Engineers (SPE), presented at the SPE Annual Technical Conference and Exhibition, Sep. 2018, 15 pages.

Chen et al., "Semicontinuous Monomer-Starved Emulsion Polymerization as a Means to Produce Nanolatexes: Analysis of Nucleation Stage," Langmuir, 29: 5650-5658, 2013, 9 pages.

Chen et al., "FITC functionalized magnetic core-shell $Fe_3O_4$/Ag hybrid nanoparticle for selective determination of molecular biothiols," Sensorts and Actuators B: Chemical 193: 857-863, 2014, 7 pages.

Christy et al., "Characterization of Natural Organic Matter by Pyrolysis/GC-MS," Environment International, 25, 1999, 9 pages.

Chuang et al., "Ultra-sensitive in-situ detection of novel near-infrared persistent luminescent tracer nanoagents in cmde oil-water mixtures," a natureresearch journal, Scientific Reports, Jun. 15, 2016, 5 pages.

Clark et al., "Water-Soluble Fluorochemical Surfactant Well Stimulation Additives," SPE9008, Society of Petroleum Engineers (SPE), Journal of Petroleum Technology, 34:07, Jul. 1982, 5 pages.

Clough et al., "Characterization of Kerogen and Source Rock Maturation Using Solid-State NMR Spectroscopy," Energy & Fuels, 2015, 29(10): 6370-6382, 42 pages.

Coates et al, "Enhancement of luminescence of europium(m) ions in water by use of synergistic chelation. Part 1.1:1 and 2:1 complexes," J. Chem. Soc, Perkin Trans. 2 (1275-1282), Jan. 1996, 8 pages.

Cole et al., "Polyethylene Glycol Modified, Cross-Linked Starch-Coated Iron Oxide Nanoparticles for Enhanced Magnetic tumor Targeting," Biomaterials, 32:8 (2183-2193), Mar. 1, 2011, 11 pages.

Constantin and Davidson, "Lamellar La mesophases doped with inorganicnanoparticles," MINIREVIEW, Chem. Phys. Chem. 15: 1270-1282, 2014, 12 pages.

Corning Incorporated, "12.10G1 Fluidic Modules Description," in 09-CD, MG1 HP Instruction Manual, 5 ed.; Corning, Ed. 78-79, 2016, 2 pages.

Corning, "The future flows through Corning Advanced Flow-Reactors," G1 Reactor. Corning, Ed. 2016, 3 pages.

Cox et al., "Pyrolyzable Nanoparticle Tracers for Environmental Interrogation and Monitoring," ACS Appl. Mater. Interfaces 9, 2017, 10 pages.

Cubillos et al., "The Value of Inter-well and Single Well Tracer Technology for De-Risking and Optimizing a CEOR Process—Caracara Field Case," SPE 174394-MS, Society of Petroleum Engineers (SPE), presented at the EUROPEC 2015, Jun. 1-4, 2015, 19 pages.

Das et al., "Molecular Fluorescence, Phosphorescence, and Chemiluminescence Spectrometry," American Chemical Society (ACS Publications), Analytical Chemistry 84: S7-625, Nov. 3, 2011, 29 pages.

Deans, "Using Chemical Tracers to Measure Fractional Flow and Saturation In-Situ," SPE-7076, Society of Petroleum Engineers (SPE), presented at SPE Symposium on improved Methods of Oil Recovery, Apr. 16-17, 1978, 10 pages.

Deschamps et al., "Drilling to the Extreme: the Micro-Coring Bit Concept," IADC/SPE 115187, Society of Petroleum Engineers (SPE), International Association of Drilling Contractors (IADC), presented at the IADC/SPE Asia Pacific Drilling Technology Conference and Exhibition, Aug. 25-27, 2008, 12 pages.

Desmette et al., "Drilling Hard and Abrasive Rock Efficiently, or Generating Quality Cuttings? You No Longer Have to Choose . . . ," SPE 116554, Society of Petroleum Engineers (SPE), presented at the 2008 SPE Annual Technical Conference and Exhibition, Sep. 21-24, 2008, 19 pages.

Doda et al., "Investigation of Alkali Resistant Polymer for Improved Heavy Oil Recovery," SPE 165514, Society of Petroleum Engineers (SPE), presented at SPE Heavy Oil Conference-Canada, Jun. 11-13, 2013, 15 pages.

Du and Guan, "Interwell tracer tests: lessons learned from past field studies," SPE 93140-MS, Society of Petroleum Engineers (SPE),

(56) References Cited

OTHER PUBLICATIONS presented at the SPE Asia Pacific Oil and Gas Conference and Exhibition, Apr. 5-7, 2005, 9 pages.

Duan et al., "Review article: Fabrication of nanofluidic devices," Biomicrofluidics, Mar. 2013, 7:2 (026501), 42 pages.

Ducros, "Source Rocks of the Middle East," Source Rock Kinetics: Goal and Perspectives. AAPG Geosciences Technology Workshop, Jul. 2016, 30 pages.

Dugstad, "Chapter 6: Well-to-well tracer tests," in Petroleum Engineering Handbook, 5: 651-683, 2007, 31 pages.

Edwards et al., "Extending the distance range accessed with continuous wave EPR with Gd3+ spin probes at high magnetic fields," The Royal Society of Chemistry, Physical Chemistry Chemical Physics (PCCP) 15:27 (11313-11326), 2013, 14 pages.

El-Aneed et al., "Mass Spectrometry, Review of the Basics: Electrospray, MALDI, and Commonly Used Mass Analyzers," Applied Spectroscopy Reviews 44:3 (210-230), Mar. 16, 2009, 22 pages.

Esmaeilzadeh et al., "Effect of ZrO2 nanoparticles on the interfacial behavior of surfactant solutions at airwater and n-heptane-water interfaces," Fluid Phase Equilibria, 2014, 361, 289-295, 7 pages.

Esumi et al., "Interaction between Zwitterionic Fluorocarbon and Anionic Surfactants in Aqueous Solutions," Langmuir, 9(358-360), 1993, 3 pages.

Fernández et al., "Evaluation of Cationic Water-Soluble Polymers With Improved Thermal Stability," SPE 93003, Society of Petroleum Engineers (SPE), presented at SPE International Symposium on Oilfield Chemistry, Society of Petroleum Engineers, Feb. 2005, 13 pages.

Fichtel et al., "A highly sensitive HPLC method for determination of nanomolar concentrations of dipicolinic acid, a characteristic constituent of bacterial endospores," Journal of Microbiological Methods, 2007, 70: 319-327, 9 pages.

Freeze and Cherry, "Chapter 9: Groundwater Contamination," in Groundwater, Englewood Cliffs, NJ: Prentice-Hall, Inc., 1979, 80 pages.

Gaillard et al., "New Water Soluble Anionic NVP Acrylamide Terpolymers for Use in Harsh EOR Conditions," SPE-169108-MS, Society of Petroleum Engineers (SPE), presented at SPE Improved Oil Recovery Symposium, Apr. 12-14, 2014, 18 pages.

Gaillard et al., "Selection of Customized Polymers to Enhance Oil Recovery from High Temperature Reservoirs," SPE-177073-MS, presented at the SPE Latin American and Caribbean Petroleum Engineering Conference, Society of Petroleum Engineers, Nov. 2015, 15 pages.

Galdiga and Greibrokk, "Ultra-trace determination of fluorinated aromatic carboxylic acids in aqueous reservoir fluids using solid-phase extraction in combination with gas chromatography-mass spectrometry," Journal of Chromatography A 793:2 (297-306), Jan. 16, 1998, 10 pages.

Gao et al., "A Surface Functional Monomer-Directing Strategy for Highly Dense Imprinting of TNT at Surface of Silica Nanoparticles," JACS Communications, Journal of American Chemical Society 129:25 (7859-7866), Jun. 2007, 8 pages.

Gardiner et al., "Chapter 1: Introduction to Raman Scattering," in Practical Raman Spectroscopy, Springer-Verlag, 1989, 9 pages.

George et al., "Modified Dipicolinic Acid Ligands for Sensitation and Europium (III) Luminescence," Inorganic Chemistry 45:4 (1739-1744), Feb. 1, 2006, 6 pages.

Georgi, et al., "Advances in Cuttings Collection and Analysis," SPWLA 34th Annual Logging Symposium, Jun. 13-16, 1993, 20 pages.

Gerami et al., "Microfluidics for Porous Systems: Fabrication, Microscopy and Applications," Transport in Porous Media, 2019, 130: 277-304, 28 pages.

Goerke et al., "Analysis of the Transfer of Radical Co-polymerisation Systems from Semi-batch to Continuous Plants," in 12th International Symposium on Process Systems Engineering and 25th European Symposium on Computer Aided Process Engineering, Elsevier B.V, Copenhagen, Denmark, 2015, 6 pages.

Gordon-Grossman et al., "W-Band pulse EPR distance measurements in peptides using Gd3+-dipicolinic acid derivatives as spin labels," Physical Chemistry Chemical Physics 13:22 (10771-10780), 2011, 10 pages.

Greenkorn, "Experimental Study of Waterflood Tracers," SPE-169, Society of Petroleum Engineers (SPE), Journal Petroleum Technology, 14(1), Jan. 1962, 6 pages.

Grutzke et al., "Heptacoordinate Heteroleptic Salan (ONNO) and Thiosalan (OSSO) Titanium(IV) Complexes: Investigation of Stability and Cytotoxicity," American Chemical Society (ACS Publications), Inorganic Chemistiy 54:14 (6697-6706), Jul. 2015, 10 pages.

Guo et al., "Crystallization in a Mixture of Solvents by Using a Crystal Modifier: Morphology Control in the Synthesis of Highly Monodisperse CaCO3 Microspheres," Angew. Chem. Int. Ed. 2006, 45:3977-3981, 5 pages.

Hagoot, "The response of interwell tracer tests in watered-out reservoirs," SPE 11131-MS, Society of Petroleum Engineers (SPE), presented at the 57th Annual Fall Technical Conference and Exhibition of the Society of Petroleum Engineers of AIME, Sep. 1982, 21 pages.

Han et al., "Application of Silver-Coated Magnetic Microspheres to a SERS-Based Optofluidic Sensor," American Chemical Society (ACS Publications), The Journal of Physical Chemistry (JPCC) 115: 6290-6296, Mar. 7, 2011, 7 pages.

He et al., "Luminescent Europium Chelates Synthesis and Fluorescence Properties," Sensors and Materials 19:2 (123-132), 2007, 10 pages.

He et al., "One-pot Facile Synthesis of Janus Particles with Tailored Shape and Functionality," Electronic Supplementary Material (ESI) for Chemical Communications, The Royal Society of Chemistry, 2011, 17 pages.

Hindle et al., "Dipicolinic acid (DPA) assay revisited and appraised for spore detection," Analyst, 1999, 124: 1599-1604, 6 pages.

Holm et al., "Synthesis, Characterization, and Light-Induced Spatial Charge Separation in Janus Graphene Oxide," American Chemical Society (ACS Publications), Chemistry of Materials (CM) 30: 2084-2092, 2018, 9 pages.

Hoteng.com [online], "Microfluidic Solutions for IOR/EOR Optimisation: Rapid and Cost Efficient EOR Screening using a Rock-On-A-Chip Approach," HOT Engineering GmbH, retrieved from URL <https://www.hoteng.eom/microfluidic-solutions/#1457967643112-9de392c4-0c28>, retrieved on Jun. 2, 2020, available on or before Mar. 2019, 8 pages.

Hou et al., "Recent advances in colloidal photonic crystal sensors: Materials, structures and analysis methods," Nano Today, 2018, 22, 132-144, 13 pages.

Hu et al, "Fabrication, properties and applications of Janus particles," Chem. Soc. Rev. 41:11 (4356-4378), 2012, Feb. 2012, 23 pages.

Hu et al., "Smart Liquid SERS Substrates based on Fe3O4/Au Nanoparticles with Reversibly Tunable Enhancement Factor for Practical Quantitative Detection," Scientific Report 4: 7204 (1-10), Nov. 2014, 10 pages.

Huseby et al., "Assessing EOR potential from partitioning tracer data," SPE 172808-MS, Society of Petroleum Engineers (SPE), presented at the SPE Middle East Oil and Gas Show and Conference, Mar. 2015, 15 pages.

Huseby et al., "High Quality Flow Information from Tracer Data," SPE-169183-MS, Society of Petroleum Engineers (SPE), presented at the SPE Bergen One Day Seminar, Apr. 2, 2014, 9 pages.

Hutchins et al., "Aqueous Tracers for Oilfield Applications," SPE-21049, Society of Petroleum Engineers (SPE), presented at SPE International Symposium on Oilfield Chemistry, Feb. 20-22, 1991, 9 pages.

Jangda et al., "Evaluation of Fluorosurfactant Performance with Super-Critical CO2 Flooding for High Salinity Carbonate Reservoirs," SPE-169725-MS, presented at the SPE EOR Conference at Oil and Gas West Asia, Society of Petroleum Engineers, Mar. 2014, 14 pages.

Jenkins et al., "Ultratrace Determination of Selected Lanthanides by Luminescence Enhancement," Analytical Chemistry 68:17 (2974-2980), Sep. 1, 1996, 7 pages.

(56) References Cited

OTHER PUBLICATIONS

Jun et al., "Multifunctional Silver-Embedded Magnetic Nanoparticles as SERS Nanoprobes and Their Applications," Wiley-VCH Verlag GmbH& Co. KGaA, Weinheim, Small 6:1 (119-125), Jan. 4, 2010, 7 pages.
Junkers, "Precision Polymer Design in Microstructured Flow Reactors: Improved Control and First Upscale at Once," Macromol. Chem. Phys. 218: 1600421-1600421, 2016, 9 pages.
Kaushik et al., "Gd(III) and Mn(II) complexes for dynamic nuclear polarization: small molecular chelate polarizing agents and applications with site-directed spin labeling of proteins," The Royal Society of Chemistry, Physical Chemistry Chemical Physics (PCCP) 18:39 (27205-27218), 2016, 36 pages.
Khan et al., "Optimizing waterflood management in a giant UAE carbonate oil field using simulation-based streamlines," SPE 171777-MS, Society of Petroleum Engineers (SPE), presented at the Abu Dhabi International Petroleum Exhibition and Conference, Nov. 10-13, 2014, 9 pages.
Kneipp et al., "Single Molecule Detection Using Surface-Enhanced Raman Scattering (SERS)," Physical Review Letters, American Physical Society 78:9, Mar. 3, 1997, 4 pages.
Knowles et al., "Zwitterion Functionalized Silica Nanoparticle Coatings: The Effect of Particle Size on Protein, Bacteria, and Fungal Spore Adhesion," Langmuir, 35(5): 1335-1345, 2019, 11 pages.
Kong et al., "Microfluidic diatomite analytical devices for illicit drug sensing with ppb-level sensitivity," Sensors and Actuators, B, 259, 2018, 9 pages.
Komberger and Thiele, "Experiences with an Efficient Rate-Management Approach for the 8th Tortonian Reservoir in the Vienna Basin," SPE 166393-PA, Society of Petroleum Engineers (SPE), presented at the SPE Annual Technical Conference and Exhibition, Sep. 30-Oct. 2, 2013, SPE Reservoir Evaluation and Engineering 17:2, May 2014, 12 pages.
Kosynkin and Alaskar, "Oil Industry First Interwell Trial of Reservoir Nanoagent Tracers," SPE 181551-MS, Society of Petroleum Engineers (SPE), presented at the SPE Annual Technical Conference and Exhibition, Sep. 2016, 15 pages.
Kramer, "Water-Soluble Dendritic Architectures with Carbohydrate Shells for the Templation and Stabilization of Catalytically Active Metal Nanoparticles," published by ACS, Macromolecules, 38:20 (8308-8315), Aug. 27, 2005, 8 pages.
Kulawardana et al., "Rheology and Transport of Improved EOR Polymers under Harsh Reservoir Conditions," SPE 154294, Society of Petroleum Engineers (SPE), presented at the SPE Improved Oil Recovery Symposium, Apr. 14-18, 2012, 14 pages.
Labbe et al., "Development of metal-chelating inhibitors for the Class II fructose 1,6-bisphosphate (FBP) aldolase," Journal of Inorganic Biochemistry 112: 49-58, Jul. 2012, 10 pages.
Larsen et al., "Efficient Synthesis of 4,7-Diamino Substituted 1,10-Phenanthroline-2,9-dicarboxamides," Organic Letters, 13:13 (3546-3548), Jul. 1, 2011, 3 pages.
Lee et al., "Site-Selective In Situ Grown Calcium Carbonate Micromodels with Tunable Geometry, Porosity, and Wettability," Advanced Functional Materials Interfaces, 2016, 10 pages.
Levitt et al., "Selection and Screening of Polymers for Enhanced-Oil Recovery," SPE 113845, Society of Petroleum Engineers (SPE), presented at the SPE Symposium on Improved Oil Recovery, Apr. 19-23, 2008, 18 pages.
Lewan, "Evaluation of petroleum generation by hydrous pyrolysis experimentation," Phil. Trans. R. Soc. Lond. A, 1985, 315: 123-134, 13 pages.
Lewan, "Experiments on the role of water in petroleum formation," Geochimica et Cosmochimica Acta, Pergamon, 1997, 61:17 (3691-3723), 33 pages.
Li et al., "Magic Angle Spinning NMR Structure Determination of Proteins from Pseudocontact Shifts," JACS Communications, Journal of the American Chemical Society 135:22 (8294-8303), May 2013, 10 pages.
Li et al., "Thiol-ene reaction: a versatile tool in site-specific labelling of proteins with chemically inert tags for paramagnetic NMR," The Royal Society of Chemistry, Chemical Communications, Cambridge, United Kingdom 48:21 (2704-2706), 2012, 18 pages.
Lomstein and Jorgensen, "Pre-column liquid chromatographic determination of dipicolinic acid from bacterial endospores," Limnology and Oceanography: Methods, Apr. 2012, 10:4, 227-233, 14 pages.
Lu et al., "Quantitative prediction of seismic rock physics of hybrid tight oil reservoirs of the Permian Lucaogou Formation, Junggar Basin, Northwest China," Journal of Asian Earth Sciences, 2019, 178:216-223, 8 pages.
Luo et al., "Nanofluid of graphene-based amphiphilic Janus Nanosheets for tertiary or enhanced oil recovery: high performance at low concentration," Proceedings of the National Academy of Sciences of USA, PNAS, vol. 113, No. 28, Jul. 12, 2016, 17 pages.
Luo et al., "Secondary Oil Recovery Using Graphene-Based Amphiphilic JanusNanosheet Fluid at an Ultralow Concentration," American Chemical Society (ACS Publications), Industrial & Engineering Chemistry Research (I&EC Research), 56: 11125-11132, Sep. 2017, 25 pages.
Manna et al., "Complexation behavior of trivalent actinides and lanthanides with 1,10-phenanthroline-2,9-dicarboxylic acid based ligands: insight from density functional theory," Physical Chemistry Chemical Physics (PCCP) 14:31 (11060), Jan. 1, 2012, 10 pages.
Mao et al., "Chemical and nanometer-scale structure of kerogen and its change during thermal maturation investigated by advanced solid-state 13C NMR spectroscopy," Geochimica et Cosmochimica Acta, 2010, 74(7): 2110-2127, 18 pages.
Marais et al., "Time-Resolved Fluorescence for Real-Time Monitoring of Both Scale and Corrosion Inhibitors: a Game-Changing Technique," SPE 179867, Society of Petroleum Engineers (SPE), presented at the SPE International Oilfield Scale Conference and Exhibition held in Aberdeen, Scotland, May 11-12, 2016 11 pages.
Marchetti et al., "Fluorous affinity chromatography for enrichment and determination of perfluoroalkyl substances," American Chemical Society (ACS Publications), Annual Review of Analytical Chemistry 84: 7138-7145, Jul. 19, 2012, 8 pages.
Martinez et al., "Chapter 9: Polysaccharide-based Nanoparticles for Controlled Release Formulations," in The Delivery of Nanoparticles, 185-222, May 2012, 39 pages.
Martini et al., "How to Monitor Scale Inhibitor Squeeze using Simple TRF Tracers," SPE-173768-MS, Society of Petroleum Engineers (SPE), presented at the SPE International Symposium on Oilfield Chemistry held in the Woodlands, Texas, Apr. 13-15, 2015, 8 pages.
McGrail et al., "Selective mono-facial modification of grapheneoxide nanosheets in suspension," The Royal Society of Chemistry, Chem. Commun, 52: 288-291, 2016, 5 pages.
Melton et al, "Complexes of Greatly Enhanced Thermodynamic Stability and Metal Ion Size-Based Selectivity, Formed by the Highly Preorganized Non-Macrocyclic Ligand 1,10-Phenanthroline-2,9-dicarboxylic Acid: A Thermodynamic and Crystallographic Study," Inorganic Chemistry 45:23 (9306-9314), Nov. 1, 2006, 9 pages.
Meyer et al., "Identification of Source Rocks on Wireline Logs by Density/Resistivity and Sonic Transit Time/Resistivity Crossplots," AAPG Bulletin, 1984, 68(2): 121-129, 9 pages.
Micronit.com [online], "Enhanced oil recovery," retrieved from URL <https://www.micronit.com/products/enhanced-oil-recovery.html>, retrieved on Mar. 10, 2020, 5 pages.
Micronit.com [online], "Lab-on-a-chip and MEMS Solutions," retrieved from URL <https://www.micronit.com/>, retrieved on Jun. 2, 2020, available on or before Mar. 19, 2018 via wayback machine URL <https://web.archive.org/web/20180319182410/https://www.micronitcom/>, 7 pages.
Miller and McQuade, "5 Synthesis of Materials I Flow—Principles and Practice," in De Gruyter et al., Flow Chemistry, 2: 133-160, 2014, Part II, Chapter 5, 28 pages.
Mohamed et al., "Reaction screening in continuous flow reactors," J. Tetrahedron Letters, 57: 3965-3977, 2016, 12 pages.
Morse et al., "Enhanced Reaction Efficiency in Continuous Flow," Isr. J. Chem, 57:218-227, Apr. 2017, 14 pages.

(56) References Cited

OTHER PUBLICATIONS

Moyner et al., "The Application of Flow Diagnostics for Reservoir Management," Society of Petroleum Engineers (SPE), SPE Journal, Apr. 2015, 18 pages.

Muller and Seubert, "Ultra trace determination of fluorobenzoic acids in tap and reservoir water using solid-phase extraction and gas chromatography-mass spectrometry," Journal of Chromatography A, 1260: 9-15, Oct. 2012, 7 pages.

Musyanovych et al., "Preparation of Biodegradable Polymer Nanoparticles by Miniemulsion Technique and Their Cell Interactions," Macromolecular Bioscience, 8:2, Feb. 11, 2008, 13 pages.

Namwong et al., "Fabricating Simple Wax Screen-Printing Paper-Based Analytical Devices to Demonstrate the Concept of Limiting Reagent in Acid-Base Reactions," Journal of Chemical Education 95:2, 2018, 5 page.

Negin et al., "Application of nanotechnology for enhancing oil recovery—A review," Ke Ai Advanced Research Evolving Science, Petroleum 2: 324-333, 2016, 10 pages.

Negin et al., "Most common surfactants employed in chemical enhanced oil recovery," Petroleum 3: 197-211, 2017, 32 pages.

Ng et al., "Graphene-based two-dimensional Janus materials," NPG Asia Materials 10:4 (217-237), Apr. 2018, 21 pages.

Nge et al., "Advances in Microfluidic Materials, Functions, Integration, and Applications," Chem. Rev., Apr. 2013, 113:4 (2550-2583), 34 pages.

Nie et al., "Probing Single Molecules and Single Nanoparticles by Surface-Enhanced Raman Scattering," Science 275:5303 (1102-1106), Feb. 21, 1997, 6 pages.

Nikonov et al., "Development of Remote Gas Condensate Fields: Challenges and Solutions," SPE 176660-MS, Society of Petroleum Engineers (SPE), SPE Russian Petroleum Technology Conference, Oct. 26-28, 2015, published Jan. 1, 2015, 21 pages.

Ogden et al., "Complexation of Am(III) and Nd(in) by 1,10-Phenanthroli ne-2,9-Di carboxylic Acid," Journal of Solution Chemistry 42:1 (211-225), 2013, 15 pages.

Ouali et al., "Analysis of Paramagnetic NMR Spectra of Triple-Helical Lanthanide Complexes with 2,6-Dipicolinic Acid Revisited: A New Assignment of Structural Changes and Crystal-Field Effects 25 Years Later," Inorganic Chemistry 41:6 (1436-1445), Feb. 2002, 10 pages.

Pallenberg et al. "Synthesis and Characterization of Some Copper(I) Phenanthroline Complexes" Inorg. Chem. 34: 2833-2840, 1995, 8 pages.

Parker and Williams, "Getting excited about lanthanide complexation chemistry," Journal of the Chemical Society, Dalton Transactions, 18: 3613-3628, 1996, 16 pages.

Parker et al., "Being excited by lanthanide coordination complexes: aqua species, chirality, excited-state chemistry, and exchange dynamics," Chemical Reviews, 102:6 (1977-2010), May 2002, 34 pages.

Peng et al., "A review of nanomaterials for nanofluid enhanced oil and recovery," The Royal Society of Chemistry, RSC Advances 7: 32246-32254, Jun. 13, 2017, 9 pages.

Petoud et al., "Brilliant SM, Eu, Tb, and Dy Chiral Lanthanide Complexes with Strong Circularly Polarized Luminescence," JACS Communications, Journal of the American Chemical Society 2017:129 (77-83), Dec. 15, 2006, 7 pages.

Potapov et al., "Nanometer-Scale Distance Measurements in Proteins Using Gd3+ Spin Labeling," Journal of the American Chemical Society, 132:26 (9040-9048), Jun. 2010, 9 pages.

Qianming et al., "Bspda Synthesis and its Europium (III) Complexes' Fluorescence," Chemical Industry Times, Jul. 2005, 19(7): 38-41, 4 pages (English Abstract).

Quadri et al., "Screening of Polymers for EOR in High Temperature, High Salinity and Carbonate Reservoir Conditions," IPTC-18436-MS, presented at the International Petroleum Technology Conference (IPTC), Dec. 6-9, 2015, 30 pages.

Rashadan et al., "Effect of the preparation route, PEG and annealing on the phase stability of Fe3O4 nanoparticles and their magnetic properties," Journal of Experimental Nanoscience 8:2 (210-222), 2013, 14 pages.

Reese et al., "Synthesis of Highly Charged, Monodisperse Polystyrene Colloidal Particles for the Fabrication of Photonic Crystals," Colloid and Interface Science, 2000, 232: 76-80, 5 pages.

Reisch and Klymchenko, "Fluorescent Polymer Nanoparticles Based on Dyes: Seeking Brighter Tools for Bioimaging." Small 12(15): 1968-1992 2016, 25 pages.

Renault et al., "Three-Dimensional Wax Patterning of Paper Fluidic Devices," Langmuir, 30:23, 2014, 7 pages.

Rowan et al., "Dynamic Covalent Chemistry," Angewante Chemie International Edition 41: 898-952, Mar. 15, 2002, 55 pages.

Sabbatini et al., "Luminescent lanthanide complexes as photochemical supramolecular devices," Coordination Chemistiy Reviews, 123:1-2 (201-228), Feb. 1993, 28 pages.

Sabhapondit et al., "Water Soluble Acrylamidomethyl Propane Sulfonate (AMPS) Copolymer as an Enhanced Oil Recovery Chemical," Energy & Fuels, 17:683-688, 2003, 6 pages.

Saeki et al., "Upper and lower critical solution temperatures in poly (ethylene glycol) solutions," Polymer, 17:8, (685-689), Aug. 1976, 5 pages.

Sajjadi, "Nanoparticles Formation by Monomer-Starved Semibatch Emulsion Polymerization," Langmuir, 23: 1018-1024, 2007, 7 pages.

Sajjadi, "Particle Formation under Monomer-Starved Conditions in the Semibatch Emulsion Polymerization of Styrene. I. Experimental.," Journal of Polymer Science: Part A: Polymer Chemistry, 39: 3940-3952, 2001, 13 pages.

Sammes and Yshioglu, "Modern bioassays using metal chelates as luminescent probes," Natural Product Reports, 31:1, 1996, 28 pages.

Sanni et al., "A field case study of inter-well chemical tracer test," SPE-173760-MS, Society of Petroleum Engineers (SPE), in SPE International Symposium on Oilfield Chemistry, Apr. 2015, 17 pages.

Sanni et al., "Pushing the envelope of residual oil measurement: A field case study of a new class of inter-well chemical tracers," Journal of Petroleum Science and Engineering 163, 2018, 19 pages.

Santarelli et al., "Formation Evaluation From Logging on Cuttings," SPE 36851, Society of Petroleum Engineers (SPE), presented at the 1996 SPE Permian Basin Oil and Gas Recovery Conference, Mar. 27-29, 1996, SPE Reservoir Evaluation and Engineering, published Jun. 1998, 7 pages.

Schmidt et al., "Copper dipicolinates as peptidomimetic ligands for the Src SH2 domain," Bioorganic & Medicinal Chemistry Letters, 14:16 (4203-4206), Aug. 2004, 4 pages.

Schmidt et al., "Synthesis of Mono- and Dinuclear Vanadium Complexes and Their Reactivity toward Dehydroperoxidation of Alkyl Hydroperoxides," Inorganic Chemistry 56:3 (1319-1332), 2017, 14 pages.

Seah et al., "Optimizing Recovery in Gas Condensate Reservoirs," SPE 171519-MS, Society of Petroleum Engineers (SPE), SPE Asia Pacific Oil and Gas Conference and Exhibition, Oct. 16, 2014, 19 pages.

Selvin et al., "Principles and biophysical applications of lanthanide-based probes," Annual Review of Biophysics and Biomolecular Structure 31: 275-302, Jun. 2002, 28 pages.

Serres-Piole et al., "Direct sensitive simultaneous determination of fluorinated benzoic acids in oil reservoir waters by ultra high-performance liquid chromatography-tandem mass spectrometry," Journal of Chromatography A, 1218, Aug. 2011, 6 pages.

Serres-Piole et al., "Water tracers in oilfield applications: Guidelines," Elsevier Ltd., Journal of Science and Engineering 98-99: 22-39, Nov. 2012, 18 pages.

ShamsiJazeyi et al., "Polymer-Coated Nanoparticles for Enhance Oil Recovery," Journal of Applied Polymer Science, 131:15, Aug. 5, 2014, 13 pages.

Sharma and Mohanty, "Wettability Alteration in High-temperature and High-salinity Carbonate Reservoirs," SPE 147306, Society of Petroleum Engineers (SPE), presented at the SPE Annual Technical Conference and Exhibition, Oct. 30-Nov. 2, 2011, SPE Journal 18:4 (646-655), Aug. 2013, 10 pages.

Shook et al., "Determining Reservoir Properties and Flood Performance from Tracer Test Analysis," SPE 124614, Society of Petroleum Engineers (SPE), presented at SPE Annual Technical Conference and Exhibition, Oct. 4-7, 2009, 19 pages.

(56) References Cited

OTHER PUBLICATIONS

Singh et al., "Paper-based sensors: emerging themes and applications," Sensors, 18:9, 2018, 22 pages.
Sobeih et al., "Recent trends and developments in pyrolysis-gas chromatography," Journal of Chromatography A, 1186:1-2 (51-66), Oct. 11, 2007, 16 pages.
Solomon et al., "Synthesis and Study of Silver Nanoparticles," Journal of Chemical Education 84:2 (332-325), 2007, 4 pages.
Song et al., "SERS-Encoded Nanogapped Plasmonic Nanoparticles: Growth of Metallic Nanoshell by Templating Redox-Active Polymer Brushes," JACS Communications, Journal of the American Chemical Society 136: 6838-6841, Apr. 28, 2014, 4 pages.
Sriram et al., "Paper-based microfluidic analytical devices for coloimetric detection of toxic ions," Trends in Analytical Chemistry, 93, Jun. 2017, 43 pages.
Stein et al., "Design and functionality of colloidal-crystal-templated materials-chemical applications of inverse opals," Chem. Soc. Rev., 2013, 42: 2763-2803, 41 pages.
Stiles et al., "Surface-Enhanced Raman Spectroscopy," Annual Review of Analytical Chemistry 1: 601-626, Mar. 18, 2008, 29 pages.
Stryer et al., "Diffusion-enhanced fluorescence energy transfer," Annual Review of Biophysics and bioengineering 11:1, 1982, 21 pages.
Su et al., "A Dipicolinic Acid Tag for Rigid Lanthanide Tagging of Proteins and Paramagnetic NMR Spectroscopy," Journal of the American Chemical Society, 130:32 (10486-10487), Jul. 2008, 2 pages.
Tang et al., "Synthesis and fluorescence properties of Tb(III) complexes with pyridine-2,6-dicarboxylic acid derivatives," Journal of Central South University of Technology (English Edition) 15:5 (599-605), Oct. 2008, 7 pages.
Tang et al., "Synthesis of Novel Derivatives of Pyridine-2,6-dicarboxylic Acid," Synthetic Communications: An International Journal for Rapid Communication of Synthetic Organic Chemistiy 36:14 (2027-2034), Jun. 2006, 9 pages.
Tang et al., "Synthesis of Eu(III) and Tb(III) Complexes with Novel Pyridine-2,6-Dicarboxylic Acid Derivatives and Their Fluorescence Properties," Front. Chem. China 4: 408-413, 2006, 6 pages.
Tathed et al., "Hydrocarbon saturation in Bakken Petroleum System based on joint inversion of resistivity and dielectric dispersion logs," Fuel, Dec. 2018, 233: 45-55, 11 pages.
Taylor et al., "Water-Soluble Hydrophobically Associating Polymers for Improved Oil Recovery: A Literature Review," SPE 29008, Society of Petroleum Engineers (SPE), Journal of Petroleum Science and Engineering, 19:3-4 (265-280), Mar. 1998, 16 pages.
Thomas et al., "Deployment and Detection of a Novel Barcoded Advanced Tracers System for the Optimization of Improved Waterflood Recovery in Hydrocarbon Reservoirs" SPE-194872-MS, SPE Middle East Oil and Gas Show and Conference. Society of Petroleum Engineers, 2019, 10 pages.
Tian et al., "Off-Resonant Gold Superstructures as Ultrabright Minimally Invasive Surface-Enhanced Raman Scattering (SERS) Probes," American Chemical Society (ACS Publications), Chemistry of Materials (CM) 27: 5678-5684, Jul. 2015, 7 pages.
Toulhoat, "Experimentation and Modelling of U, Th and Lanthanides Transport in Fissured Rocks: Influence of Complexation," MRS Proceedings 50, Jan. 1, 1985, 8 pages.
Trippetta et al., "The seismic signature of heavy oil on carbonate reservoir through laboratory experiments and AVA modelling," Journal of Petroleum Science and Engineering, 2019, 177: 849-860, 12 pages.
Vaccaro et al., "Flow Approaches Towards Sustainability," Green Chem, 16:3680-3704, 2014, 25 pages.
Vatanparast et al., "Wettability alteration of low-permeable carbonate reservoir rocks in presence of mixed ionic surfactants," Petroleum Science and Technology 29:18 (1873-1884), 2011, 14 pages.
Vermolen et al., "Pushing the Envelope for Polymer Flooding Towards High-temperature and High-salinity Reservoirs with Polyacrylamide Based Terpolymers," SPE 141497, Society of Petroleum Engineers (SPE), presented at SPE Middle East Oil and Gas Show and Conference, Mar. 20-23, 2011, 9 pages.
Vollrath et al., "Fluorescence imaging of cancer tissue based on metal-free polymeric nanoparticles—a review." J. Mater. Chem. B 1:15 (1994-2007), 2013, 15 pages.
Wagner, "The Use of Tracers in Diagnosing Interwell Reservoir Heterogeneities—Field Results," SPE-6046, Society of Petroleum Engineers (SPE), Journal of Petroleum Technology, Nov. 1997, 7 pages.
Walther et al, "Janus Particles: Synthesis, Self-Assembly, Physical Properties and Applications," American Chemical Society (ACS Publications), Chem. Rev. 113:7 (5194-5261), Apr. 2013, 68 pages.
Wampler, "Chapter 1: Applied pyrolysis: anoverview," Applied Pyrolysis Handbook, 2007, 26 pages.
Wang et al., "The Design and Implementation of a Full Field Inter-Well Tracer Program on a Giant UAE Carbonate Oil Field," SPE-177527-MS, Society of Petroleum Engineers (SPE), in Abu Dhabi International Petroleum Exhibition and Conference, Nov. 2015, 8 pages.
Wang et al., "Toward Reservoir on a Chip: Fabricating Reservoir Micromodels by in Situ Growing Calcium Carbonate Nanocrystals in Microfluidic Channels," ACS Applied Materials and Interfaces, 2017, 21 pages.
Wever et al., "Polymers for enhanced oil recovery: A paradigm for structure-property relationship in aqueous solution," Progress in Polymer Science, 36:11 (1558-1628), Nov. 2011, 71 pages.
Wu et al., "Development of New Polymers with Better Performance under Conditions of High Temperature and High Salinity," SPE 155653, Society of Petroleum Engineers (SPE), presented at the SPE EOR Conference at Oil and Gas, Apr. 16-18, 2012, 11 pages.
Wu et al., "A reusable biosensor chip for SERS-fluorescence dual mode immunoassay," Proc. SPIE 9543: 954317-1, presented at the Third International Symposium on Laser Interaction with Matter (LIMIS), May 4, 2015, 6 pages.
Wu et al., "A SERS-Assisted 3D Barcode Chip for High-Throughput Biosensing," Material Views Full Papers, Small Journal 11:23 (2798-2806), Jun. 11, 2015, 9 pages.
Xu et al., "Measurement of two-photon excitation cross sections of molecular fluorophores with data from 690 to 1050 mu," Journal of the Optical Society of America B 13:3, Mar. 1996, 11 pages.
Yang et al., "The Co-Luminescence Groups of Sm—La-pyridyl Carboxylic Acids and the Binding Characteristics between the Selected Doped Complex and Bovine Serum Albumin," Bulletin of the Korean Chemical Society 33:4 (1303-1309), Apr. 20, 2012, 7 pages.
Yang et al., "Paramagnetic labeling of proteins and pseudocontact shift in structural biology," Chinese Journal of Magnetic Resonance, 2014, 31:2 (155-171), English Abstract.
Ye et al., "Synthesis and Characterization of a Water-Soluble Sulfonates Copolymer of Acrylamide and N-Allylbenzamide as Enhanced Oil Recovery Chemical," Journal of Applied Polymer Science, 128:3, (2003-2011), May 5, 2013, 9 pages.
Yun et al., "Toward Reservoir on a Chip: Rapid Performance Evaluation of Enhanced Oil Recovery Surfactants for Carbonate Reservoirs Using a Calcite-Coated Micromodel," Nature Scientific Reports, 2020, 12 pages.
Zamberi et al., "Improved Reservoir Surveillance Through Injected Tracers in a Saudi Arabian Field: Case Study," SPE 166005, Society of Petroleum Engineers (SPE), presented at the SPE Reservoir Characterization and Simulation Conference and Exhibition, Sep. 16-18, 2013, 15 pages.
Zemel, "Chapter 3: Tracers in the Oil Field," in Tracers in the Oil Field, Technology and Engineering, Elsevier 43, Jan. 1995, 47 pages.
Zhang et al., "Effect of Concentration on HPAM Retention in Porous Media," SPE-166265-PA, Society of Petroleum Engineers (SPE), presented as SPE Annual Technical Conference and Exhibition, 373-380, Sep. 30-Oct. 2, 2013, 11 pages.
Zhang et al., "Janus Particles: Synthesis, Self-Assembly, Physical Properties, and Applications," American Chemical Society (ACS Publications), Langmuir 33: 6964-6977, 2017, 14 pages.

(56) References Cited

OTHER PUBLICATIONS

Zhang et al., "Novel zwitterionic surfactant derived from castor oil and its performance evaluation for oil recovery," Colloids Surfaces A: Physicochemical and Engineering Aspects 483: 87-95, 2015, 42 pages.
Zhang et al., "Geomaterial-Functionalized Microfluidic Devices Using a Universal Surface Modification Approach," Advanced Material Interfaces, 2019, 6:23, 16 pages.
Zhao et al., "Chromatographic Separation of Highly Soluble Diamond Nanoparticles Prepared by Polyglycerol Grafting," Angewandte Chemie International Edition, 50:6 (1388-1392), Feb. 7, 2011, 5 pages.
Zhou et al., "Upconversion luminescent materials: advances and applications," American Chemical Society (ACS Publications), Chemical Reviews, 115: 395-465, Jan. 14, 2015, 71 pages.
International Search Report and Written Opinion in International Appln. No. PCT/US2022/013324, dated May 20, 2022, 16 pages.
Wang et al., "Macroporous materials: microfluidic fabrication, functionalization and applications," Chem. Soc. Rev., 2017, 45: 855-914, 60 pages.
Zhang et al., "Geo-material surface modification of microchips using layer-by-layer (LbL) assembly for subsurface energy and environmental applications," Royal Society of Chemistry, 2018, 18:285-295, 11 pages.

\* cited by examiner

MICROFLUIDIC CHIP WITH MIXED POROSITIES FOR RESERVOIR MODELING

BACKGROUND

Hydrocarbons (for example, oil, natural gas, or combinations of them) entrapped in formations can be raised to the surface, that is, produced, using wells formed through the formations. Usually, the hydrocarbons are entrapped in the formations under pressure sufficient to flow the hydrocarbons through pores of the formations into the wells. Formations can be of different types, for example, carbonate or sandstone, and can have different porosities that affect the flow of the hydrocarbons through the formations. Modeling fluid flow through reservoirs allows for improving efficiency in extracting hydrocarbons from reservoirs.

SUMMARY

An embodiment disclosed herein provides a method for modeling a reservoir with a microfluidic chip having mixed porosities.

Certain aspects of the subject matter described herein can be implemented as a method including mixing spherical grains and sacrificial particles in a suspension. The sacrificial particles are larger than the spherical grains. The suspension is injected into a channel in a microfluidic chip, and the spherical grains form microporous structures in the channel. The microporous structures are sintered in the channel. A solvent is injected into the channel, and the solvent dissolves the sacrificial particles and forms macropores between at least some of the microporous structures, thereby forming a mixed-porosity microfluidic chip.

An aspect combinable with any of the other aspects can include the following features. The mixed-porosity microfluidic chip is used to model a subsurface reservoir.

An aspect combinable with any of the other aspects can include the following features. The reservoir is a carbonate reservoir characterized by bi-modal porosity.

An aspect combinable with any of the other aspects can include the following features. Modeling the subsurface reservoir includes studying rock-fluid interactions.

An aspect combinable with any of the other aspects can include the following features. Modeling the reservoir includes spectroscopic studies of interactions between fluids and surfaces.

An aspect combinable with any of the other aspects can include the following features. Modeling the subsurface reservoir includes studying oil-water phase behavior in the pores of the mixed-porosity microfluidic chip.

An aspect combinable with any of the other aspects can include the following features. The microfluidic chip is an optically transparent or translucent chip.

An aspect combinable with any of the other aspects can include the following features. The spherical grains are calcium carbonate spheres.

An aspect combinable with any of the other aspects can include the following features. The method further includes synthesizing the calcium carbonate spheres.

An aspect combinable with any of the other aspects can include the following features. The sacrificial particles are sodium chloride crystals and the solvent is water.

An aspect combinable with any of the other aspects can include the following features. The microporous structures comprise micropores between spherical grains, and the average width of the macropores is at least about ten times larger than the average width of the micropores.

An aspect combinable with any of the other aspects can include the following features. The calcium carbonate spheres are from about 25 nanometers to about 25 microns in diameter.

An aspect combinable with any of the other aspects can include the following features. The sodium chloride crystals have a width of about 10 microns to about 250 microns.

Certain aspects of the subject matter described here can be implemented as a mixed-porosity microfluidic chip that includes a microchannel etched in a substrate. The microporous structures comprising calcium carbonate spheres sintered in the microchannel. The chip further includes macropores between at least some of the microporous structures. The average width of the macropores is at least about ten times larger than the average diameter of the calcium carbonate spheres.

An aspect combinable with any of the other aspects can include the following features. The microporous structures comprise micropores between the calcium carbonate spheres, and the average width of the macropores is at least about ten times larger than the average width of the micropores.

An aspect combinable with any of the other aspects can include the following features. The calcium carbonate spheres are from about 25 nanometers to about 25 microns in diameter.

An aspect combinable with any of the other aspects can include the following features. The macropores have a width of about 10 microns to about 250 microns.

An aspect combinable with any of the other aspects can include the following features. The mixed-porosity microfluidic chip is optically transparent or translucent.

An aspect combinable with any of the other aspects can include the following features. The microchannel has a width of from about 500 microns to about 1500 microns and a height of from about 50 microns to about 500 microns.

An aspect combinable with any of the other aspects can include the following features. The macropores are substantially cubic in shape.

The details of one or more implementations of the subject matter of this disclosure are set forth in the accompanying drawings and the description. Other features, aspects, and advantages of the subject matter will become apparent from the description, the drawings, and the claims.

DETAILED DESCRIPTION

To increase oil recovery efficiency, it is important to better understand multiphase fluid behaviors and interactions among oil-water-rock phases in underground oil reservoirs.

Carbonate reservoirs hold a significant proportion of the world's oil reserves. In a carbonate reservoir, large quantities of crude oil may be stored in microscale or nanoscale pores, and may be difficult to recover with conventional methods. Furthermore, the porosity of some carbonate reservoirs may be complex.

Some carbonate reservoirs exhibit both microporosity (defined herein as pore diameters less than about 10 microns) and also macroporosity (defined herein as a pore diameter greater than about 10 microns). In some reservoirs exhibiting both microporosity and macroporosity, the porosity can be distinctly bimodal, with microporosity pores about tens up to one thousand times tighter and smaller than the macroporosity pores. For example, in some bimodal carbonates of the Arabian Peninsula, a majority of the porosity can be attributed to two distinct fractions: a first fraction attributable to pores of between about 100 and about 1000 nm in diameter, and a second fraction attributable to pores of tens to hundreds of micrometers in diameter.

In the field of research about oil reservoirs and improved oil recovery (IOR) and enhanced oil recovery (EOR), it is desirable to have a micromodel that resembles the complicated porosities of natural carbonate reservoirs. Reservoir micromodels—sometimes referred to as "reservoir-on-a-chip"—have been used to mimic the underground oil-reservoir environment for multi-phase flow studies, enhanced oil recovery, and reservoir network mapping. However, existing micromodels may be limited in their usefulness in modeling reservoirs that may have multiple porosities in the same rock. Furthermore, typical micromodels made of glass or polymer materials may not be representative of the geochemical surface of carbonate reservoir rocks.

Generally, in accordance with the embodiments described in the present disclosure, a microfluidic chip with mixed porosities can be fabricated and utilized for such modeling purposes. The method of fabrication can include synthesizing nanoscale-sized calcium carbonate ($CaCO_3$) spheres and also micron-scale sacrificial particles, such as sodium chloride (NaCl) crystals. The calcium carbonate spheres and sacrificial particles are mixed together in a suspension. The suspension is then injected into a channel in a microfluidic chip, such that the calcium carbonate spheres form microporous structures in the channel, surrounding the sacrificial particles. After sintering, a solvent is injected into the channel to dissolve the sacrificial particles, thus forming macropores between the microporous structures.

The method allows for tuning of particle size(s) and resulting porosities, such that the resulting chip can more closely correspond to the characteristics of natural carbonate reservoirs. The resulting chip can be used to study oil-water phase behavior and rock-fluids interactions of matrices featuring both microporosity and macroporosity, with small volume of samples at low cost. The surface of the resulting chip is optically transparent or translucent and allows to directly visualize fluid behaviors near the surface by advanced spectroscopic and imaging techniques, providing useful information for enhanced oil recovery.

Figure 1:
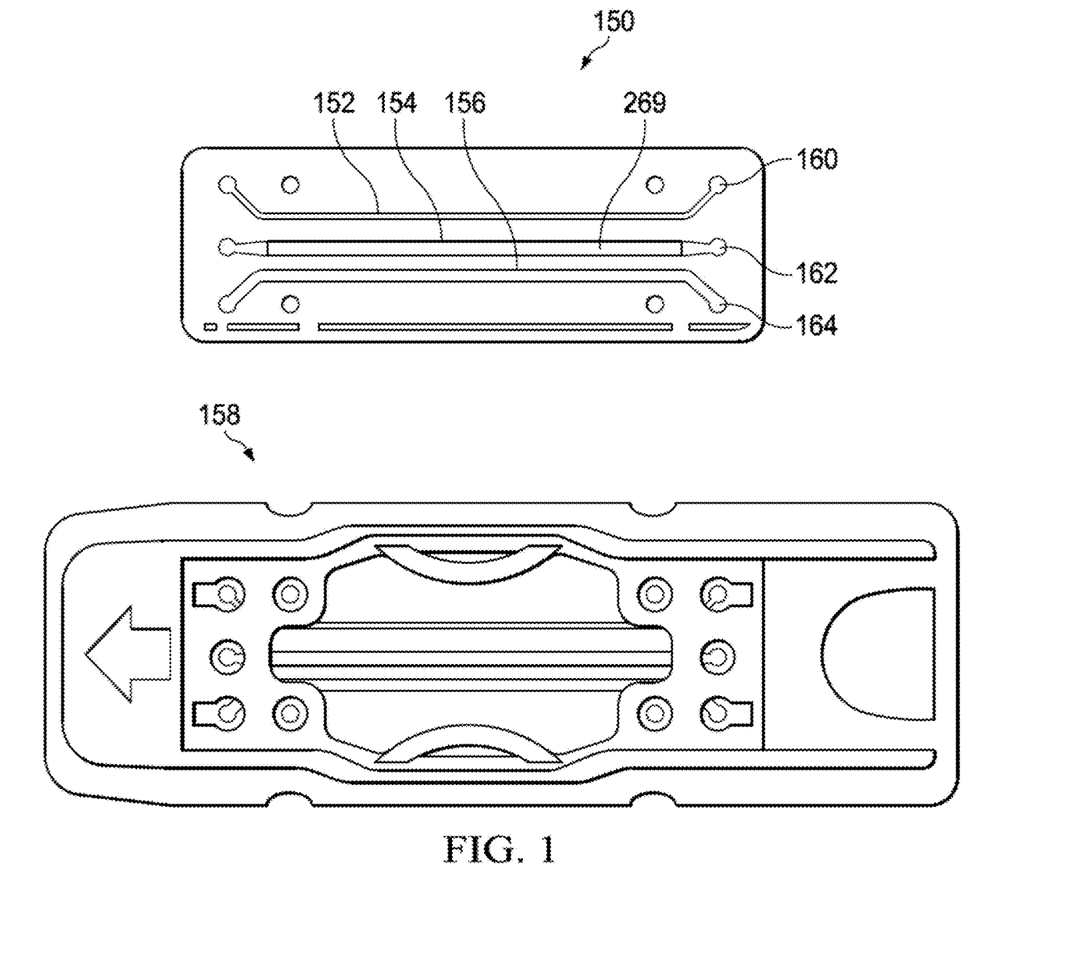
FIG. 1 is a drawing of an exemplary microfluidic chip having straight channels suitable as a component in an embodiment of the present disclosure.

FIG. 1 shows straight-channel microfluidic chip 150 of a type available from Micronit Company of the Netherlands and provides a suitable component for an embodiment of the present disclosure. Chip 150 has a length of about 45 mm, a width of about 15 mm, and a thickness of about 1245 μm. Chip 150 is comprised of borosilicate glass and has three channels 152, 154, and 156 having of width of 500 μm, 1500 μm, and 1000 μm, respectively, with each channel having a height of 50 μm. In some embodiments, the height of the channels can vary from about 50 μm to about 500 μm. Chip 150 is optically transparent and fits into a housing 158 that can, in turn, fit into a chip holder (not shown). Particles corresponding to natural sedimentary rock grains and other substances can be injected into one or more of channels 152, 154, and 156 via injection holes 160, 162, and 164, respectively, to form granular or other structures which resemble natural reservoirs in geometry, composition, or other characteristics. In accordance with an embodiment of the present disclosure, chip 150 can include mixed-porosity structures 269 comprising macropores between microporous structures sintered in one or more of the channels (for example, channel 154), as described in more detail in FIGS. 2A and 2B.

Other embodiments of the present disclosure can utilize chips of other suitable sizes, channel geometries, porosities, and other characteristics, available from various commercial suppliers.

Figure 2A:
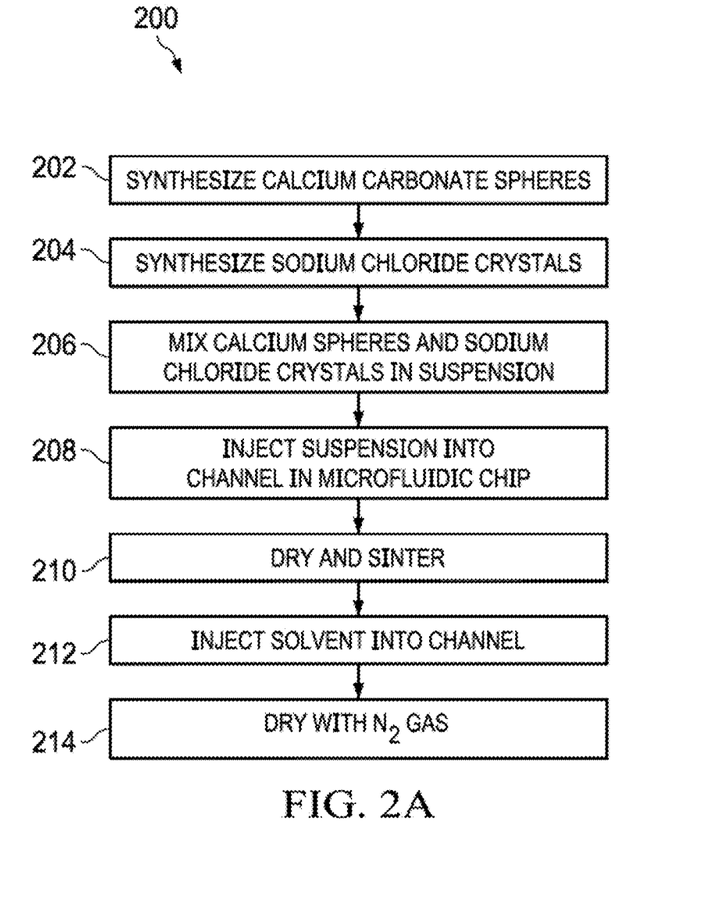
FIG. 2A is a process flow diagram of a method for fabricating a microfluidic chip having mixed porosities in accordance with an embodiment of the present disclosure.
Figure 2B:
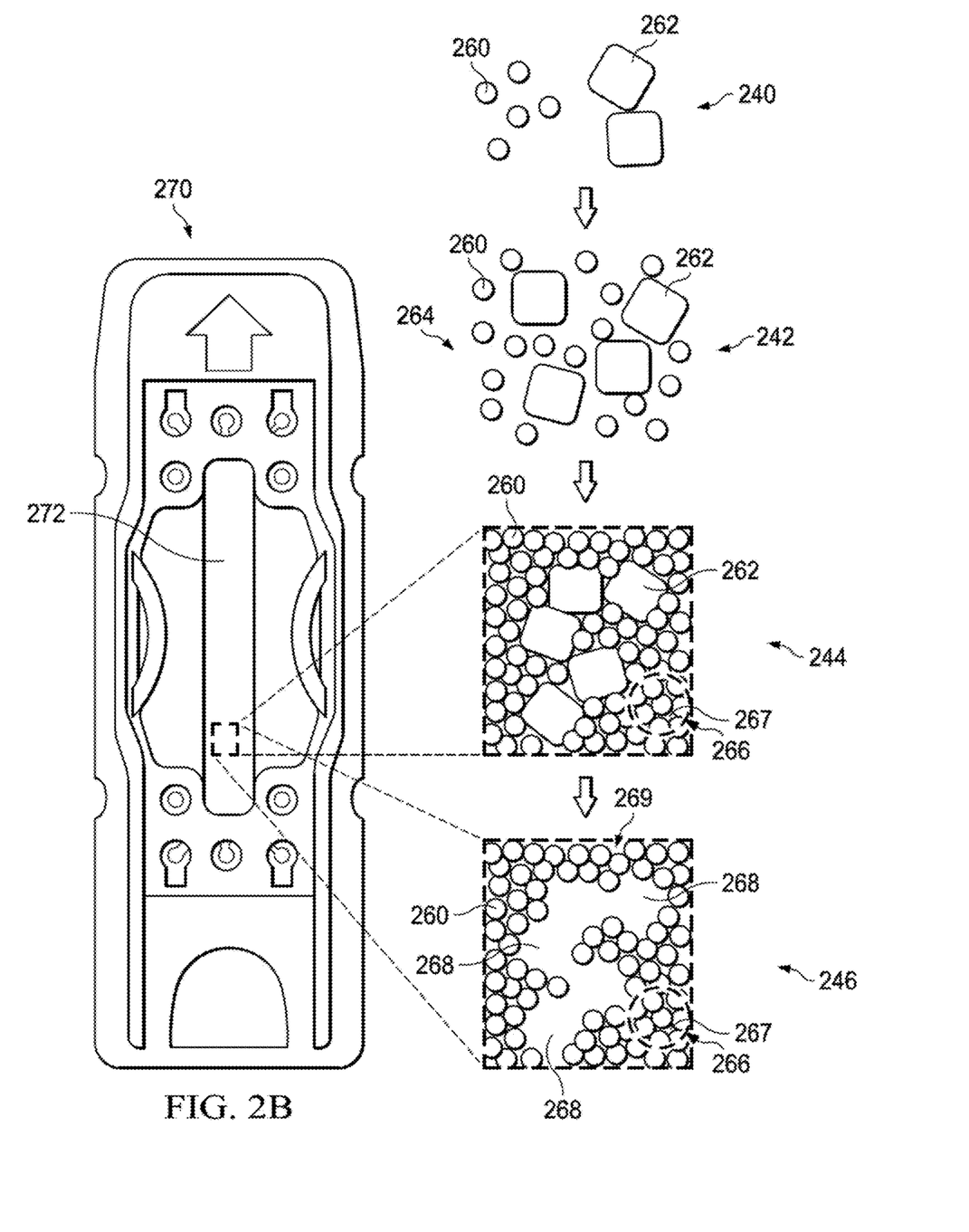
FIG. 2B is a schematic diagram of a method for fabricating a microfluidic chip having mixed porosities in accordance with an embodiment of the present disclosure.

FIG. 2A is a process flow diagram of a method 200 for fabricating a microfluidic chip having mixed porosities in accordance with an embodiment of the present disclosure. FIG. 2B is a schematic diagram illustrating some of the steps of the method described in reference to FIG. 2A. The method of FIG. 2A will be described with reference to FIG. 2B. FIG. 2B is not drawn to scale.

The method begins at block 202 with the synthesis of calcium carbonate ($CaCO_3$) spheres of a desired size. The calcium carbonate spheres can be synthesized in accordance with one or more of the methods described in the Examples section below, or via another suitable method. In one embodiment, the calcium carbonate spheres have a substantially uniform size and a diameter of about 25 nm to about 25 μm.

The calcium carbonate spheres synthesized in accordance with block 202 of FIG. 2A correspond to grains 260 at step 240 of FIG. 2B. Synthesized calcium carbonate grains can serve as a proxy for natural calcium carbonate grains and thus are suitable for creating microfluidic chips for modeling of carbonate reservoirs. In other embodiments, for example for modeling of other reservoir types, particles or grains of another composition (for example, dolomite (calcium magnesium carbonate, $CaMg(CO_3)_2$) or sandstone (silicon dioxide, $SiO_2$) particles) of a spherical or other shape (oblong, cubic, needle-shaped, or other suitable shape) can be utilized for grains 260 instead of calcium carbonate spheres. In some embodiments, grains 260 can comprise a mixture of particle compositions and/or shapes. In some embodiments, particles of a suitable composition, shape, or size may be purchased commercially instead of synthesized.

At block 204 of FIG. 2A, sodium chloride crystals of a desired size are synthesized. The sodium chloride (NaCl) crystals can be synthesized in accordance with the methods described in the Examples section below, or via another suitable method. In one embodiment, the sodium chloride crystals with width of about 10 microns to about 50 microns.

The sodium chloride crystals synthesized in accordance with block 204 of FIG. 2A correspond to sacrificial particles 262 at step 240 of FIG. 2B. Sodium chloride crystals are typically cubic in shape. In other embodiments, sacrificial particles 262 can comprise particles of a different composition, readily dissolvable with a suitable solvent. For example, alternative sacrificial particles can include $MX_2$ (M=K, Na, Cs; X=Cl, Br, $NO_3$) or $MX_2$ (M=Zn, Cu, Co, Ni, Fe, Mn, Cd; X=Cl, $NO_3$), which are water soluble. In some embodiments, sacrificial particles 262 can comprise a mixture of particle compositions and/or shapes. In some embodiments, sacrificial particles of a suitable composition, shape, or size may be purchased commercially instead of synthesized.

At block 206 of FIG. 2A, and as illustrated at step 242 of FIG. 2B, the grains 260 are mixed with sacrificial particles 262 in the desired ratio into a suspension 264. Suspension 264 comprises a suitable fluid phase to carry grains 260 and sacrificial particles 262. The fluid phase can comprise ethanol, acetone, hexane, chloroform, or another suitable fluid phase.

In one embodiment, the desired ratio of grains 260 to sacrificial particles 262 depends on the amount of microporosity of the carbonate reservoir which the chip is intended to model. For example, in Middle East carbonate reservoirs it is common to have 20% microporosity, with values of microporosity up to 50% having been observed. Furthermore, as the ratio of grains 260 to sacrificial particles 262 increases, the mechanical stability of the resulting 3D microstructures (see below) tends to increase. In one embodiment of the present disclosure, to model a carbonate reservoir having about 25-30% microporosity would correspond to a volume ratio of about 2-to-1 of grains 260 to sacrificial particles 262.

At block 208 of FIG. 2A, and as illustrated at step 244 of FIG. 2B, the suspension 264 is injected into a channel 272 of a microfluidic chip 270. Microfluidic chip 270 may correspond to chip 150 of FIG. 1 or may be another suitable microfluidic chip. A paper filter can be placed at the end of the channel to block the particles from flowing out. In one embodiment, the suspension is injected continuously until the channel is fully packed with solid particles.

Settling within channel 272, grains 260 form granular structures 266 having micropores 267 comprising the voids between the spheres and having a porosity dependent on grain shape and size. For example, calcium carbonate spheres can form granular structures comprising 3D microstructures with random close packing (RCP). For spheres with substantially uniform sizes in a 3D RCP structures, the micropores 267 are substantially tetrahedral or octahedral in shape and have a width of about 22.5% to 41.4% of the diameter of the spheres. For example, in one embodiment, spheres with a diameter of about 25 nm to about 25 μm can form a granular structure 266 with micropores 267 with a width of about 10 nm to about 10 μm. Sacrificial particles 262 are distributed among and between granular structures 266.

At block 210 of FIG. 2A, chip 270 is placed in an oven and sintered. In one embodiment wherein the grains 260 comprise calcium carbonate spheres, chip 270 is sintered at 250° C. for about two hours. At this temperature, calcium carbonate spheres are immobilized to form a robust porous structure without substantially changing the size or morphology of the spheres. Nitrogen gas is then flowed through channel 272 to dry the structures 266. The sintering process substantially immobilizes the spheres and stabilizes the structure so that it remains intact without collapsing. The sintering process may also cause some cracks among the assembled calcium carbonate sphere structures due to slight shrinking of the spheres. In one embodiment, cracks induced by thermal shrinking of calcium carbonate spheres are of a similar or smaller than the size of the spheres. The chip is removed from the oven and allowed to cool to room temperature.

At block 212 of FIG. 2A, deionized water or another suitable solvent is injected into the channel. The deionized water dissolves the sodium chloride crystals and flushes out the dissolved $Na^+$ and $Cl^-$ ions as well other ionic impurities. At block 214, nitrogen ($N_2$) gas or another suitable drying medium is flowed through the channel to dry the particle structures which remain in the channel.

Step 246 of FIG. 2B illustrates chip 270 after the solvent has been injected into chip 270 and the chip dried and made ready for use as a reservoir micromodel. Grains 260 remain in granular structures 266. As the sacrificial particles 262 dissolve, macropores 268 are left in their place between and among granular structures 266. For example, in one embodiment, sacrificial particles 262 having a width of about 10 μm to about 250 μm can result in macropores 268 having a width of about 10 μm to about 250 μm. In an embodiment wherein grains 260 are nanoscale or microscale particles and the sacrificial particles are micron-scale, the macropores 268 between the granular structures 266 result in mixed porosity structures 269 within channel 272, with voids of macroporosity (from macropores 268 resulting from dissolution of sacrificial particles 262) among and between the regions of microporosity (from micropores 267) formed by the granular structures 266.

The resulting mixed-porosity microfluidic chip remains optically transparent or translucent, allowing interactions between fluids and the surfaces to be directly visualized by multiple characterization tools, such as advanced spectroscopic and/or microscopic techniques, providing useful information for enhanced oil recovery. By injecting oil, water, and other fluids into the chip, oil-water phase behavior and the interactions between fluids and surfaces, such as rock-fluid interactions, can be observed and studied.

The ratios, composition, sizes, and shapes of grains 260 and sacrificial particles 262 can be tuned so as to result in a micromodel that corresponds to specific natural reservoirs. For example, in one embodiment, grains 260 comprise calcium carbonate spheres with a diameter of about 500 nm to about 2500 nm and sacrificial particles 262 comprise sodium chloride crystals with width of about 10 microns to about 50 microns, with the suspension mixture comprising about 50% sodium chloride crystals (with the remainder of the suspension mixture comprising the calcium carbonate spheres) and with resulting random close packing of granular structures 266. In such an embodiment, the resulting chip is characterized by a bimodal porosity similar to that found in, for example, the Arab-D formation of the Arabian Peninsula, with pore diameters in the granular structures 266 of between about 100 and to about 1000 nanometers and macroporosity resulting from macropores 268 (with widths corresponding to the width of the sacrificial particles 262).

EXAMPLES

Synthesis of Calcium Carbonate Particles and Calcium Magnesium Carbonate Particles Calcium carbonate crystals or particles can be chemically synthesized through the following reaction:

$$CaCl_2 + Na_2CO_3 \rightarrow CaCO_3(s) + 2NaCl$$

Calcium magnesium carbonate crystals or particles can be chemically synthesized through the following reaction:

$$CaCl_2) + MgCl_2 + 2Na_2CO_3 \rightarrow CaMg(CO_3)_2(s) + 4NaCl$$

In an embodiment of the present disclosure, a solution precipitation method can be used to synthesize calcium carbonate or calcium magnesium carbonate particles with sizes varying from 20 nm-20 μm with a narrow size distribution.

In a synthesis process in accordance with this embodiment, 20.3 g calcium chloride ($CaCl_2 \cdot 6H_2O$) and 14.7 g magnesium chloride ($MgCl_2 \cdot 2H_2O$) was dissolved in 100 mL deionized (D.I.) water, one part of the solution and 21.2 g sodium carbonate ($Na_2CO_3$) was dissolved in another part of the solution. The two parts of the solutions were rapidly mixed with vigorous stirring with a 1:1:2 molar ratio of $Ca^{2+}$, $Mg^{2+}$ to $CO_3^{2-}$. The reaction mixture was then transferred into an autoclave and heated at 180° C. for 12 hours. After cooling down to room temperature, the formed particles can be separated from the suspension by centrifuge and washed by water and ethanol in turn to remove impurities. Finally, the purified calcium magnesium carbonate particles are redispersed in absolute ethanol. The shape of resulting calcium carbonate particles is spherical with a narrow size distribution. By changing the concentration of $Ca^{2+}$, $Mg^{2+}$ and $CO_3^{2-}$ ions used in the synthesis, $CaCO_3$ or $Ca_{1-x}Mg_x(CO_3)_2$ spheres with different sizes in 1-25 μm can be obtained.

Figure 3A:
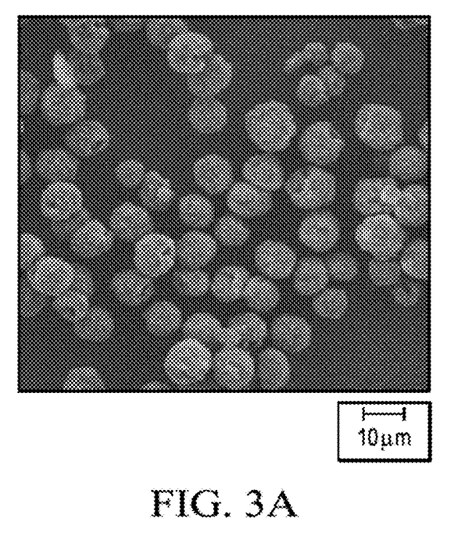
FIG. 3A-3C are scanning electron micrographs of synthesized calcium carbonate spheres in accordance with an embodiment of the present disclosure.

FIG. 3A is an SEM image of calcium carbonate spheres synthesized in accordance with the microemulsion method described in reference to block 202 of FIG. 2A. The spheres of FIG. 3A have a diameter of about 10 μm, which provides pores of about 2.25 μm to about 4.14 μm in size (about 22.5% to 41.4% of the size of the spheres) in a random close packing configuration. The SEM image of FIG. 3A was taken by scanning electron microscopy (SEM, JEOL 7100,) at 15 kV, and no additional coating was applied onto the sample surface.

In an embodiment of the present disclosure, a microemulsion can be used as a template medium to synthesize calcium carbonate particles with sizes varying from 20 nm-2000 nm with a narrow size distribution.

A microemulsion medium can be comprised of:
Igepal CO-720 (surfactant), 27.5 g
Hexanol (cosurfactant), 22 mL
$H_2O$, 13.75 mL
Cyclohexane, 170 mL In a synthesis process in accordance with this embodiment, calcium chloride ($CaCl_2$)) was dissolved in one part of the microemulsion and sodium carbonate ($Na_2CO_3$) was dissolved in another part of the microemulsion. The two parts of the microemulsions were rapidly mixed with vigorous stirring with a 1:1 $Ca^{2+}$ to $CO_3^{2-}$ molar ratio. Then, with mild stirring, the reaction completes in approximately two (2) hours and the formed particles can be separated from the microemulsion and washed by water and ethanol in turn to remove adsorbed surfactant and impurities. Finally, the purified calcium carbonate particles are redispersed in absolute ethanol. The shape of resulting calcium carbonate particles is spherical with a narrow size distribution.

Figure 3B:
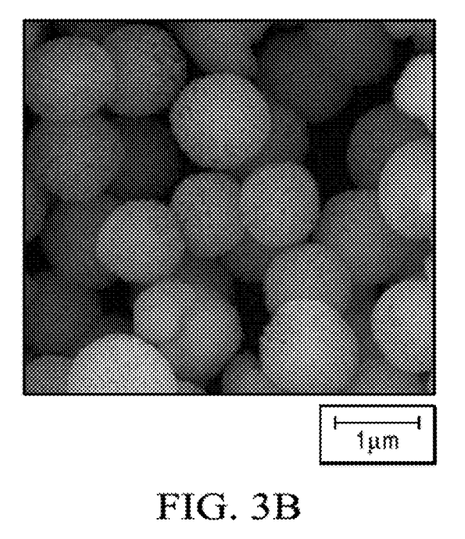

FIG. 3B is another SEM image of calcium carbonate spheres synthesized in accordance with the microemulsion method described in reference to block 202 of FIG. 2A. The spheres of FIG. 3B have a diameter of about 1000 nm, which provides pores of about 225 nm to about 414 nm in size in a random close packing configuration. The SEM image of FIG. 3B was taken by scanning electron microscopy (SEM, JEOL) at 15 kV, and no additional coating was applied onto the sample surface.

Calcium carbonate spheres with sizes from about 50 nm to 10 μm can also be synthesized by reaction of $Ca^{2+}$ ions in mixed solvent (such as $DMF-H_2O$ or alcohol-$H_2O$) with or without polymer as stabilizer, and vapor of solid $(NH_4)_2CO_3$.

In an embodiment of the present disclosure, 10 mg polymer polyacrylic acid (PAA, MW=2000) and 1 mL of 0.1M $CaCl_2$) aqueous solution were mixed in 10 mL isopropanol in a reaction vessel (50 mL beaker).

The reaction vessel was covered with parafilm, which was punctured with 6 needle holes, and placed into a desiccator at room temperature. A Petri dish (OD: 10 cm) filled with 5 g crushed ammonium carbonate and covered with parafilm punctured with 10 needle holes were also placed around the beaker in the closed desiccator. The parafilm is then removed and the precipitates in beaker were collected by centrifuge and rinsed with DI water and ethanol, and then allowed to dry at room temperature.

Figure 3C:
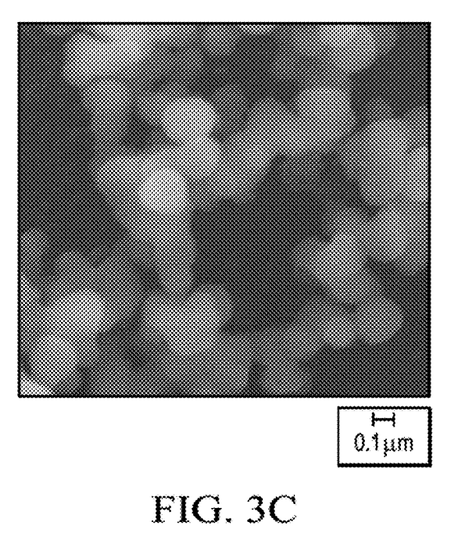

FIG. 3C is an SEM image of calcium carbonate spheres synthesized in accordance with the PAA crystal modifier method described in reference to block 202 of FIG. 2A, with a solvent mixture of DMF:H2O=1:1. The spheres of FIG. 3C have a diameter of about 200 nm, which provides pores of about 45 nm to about 82.5 nm in size in a random close packing configuration. The SEM image of FIG. 3C was taken by scanning electron microscopy (SEM, JEOL) at 15 kV, and no additional coating was applied onto the sample surface.

Figure 3D:
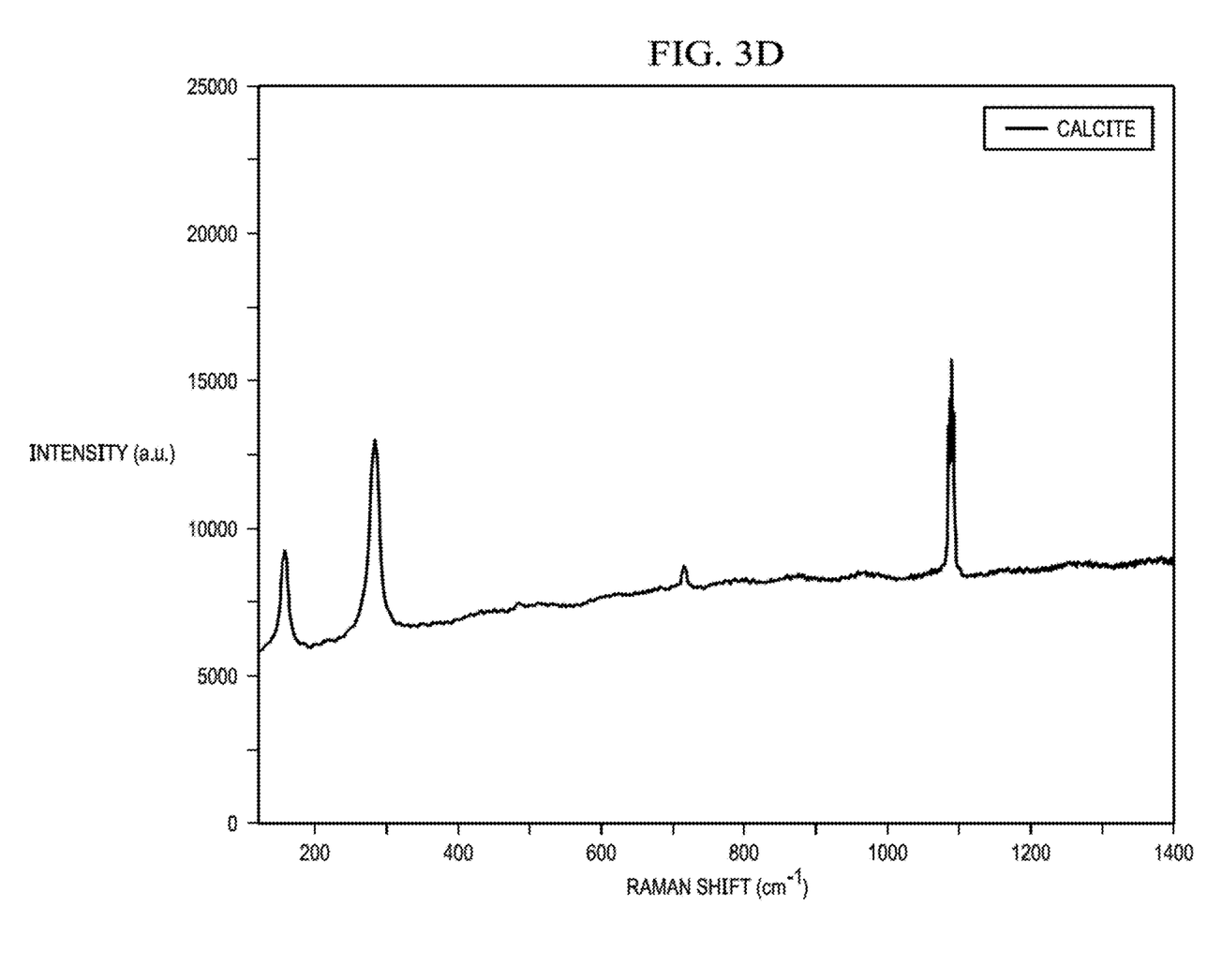
FIG. 3D is a Raman spectrum of synthesized calcium carbonate sphere in accordance with an embodiment of the present disclosure.

FIG. 3D is an exemplary Raman spectrum (Horiba, LabRAM HR Evolution) of the calcium carbonate spheres synthesized in accordance with the solution precipitation method. The $CaCO_3$ spheres prepared by the solution-vapor reaction method and the microemulsion template method also exhibit the same vibrational bands in their Raman spectra.

Synthesis of Sodium Chloride Crystals

Laboratory-synthesized sodium chloride crystals are typically cubic in shape. By using a supersaturated solution and alcohol to crystalize sodium chloride, the size of the crystals can be controlled. Sodium chloride can be first dissolved in hot water until saturate concentration is reached and then cooled down to room temperature to form a supersaturated solution. Upon introducing alcohol to the solution, crystals of sodium chloride precipitate gradually. The sizes of the sodium chloride crystals depend on the amount and type of alcohols added to the solution. Available alcohols include, for example, ethanol, n-propanol, isopropanol, n-butanol, 2-butanol or pentanol, and resulting sizes of NaCl cubes can be controlled in the range of 500 nm-500 μm. Sodium chloride crystals of the desired size can be separated and collected by centrifuge.

Figure 4A:
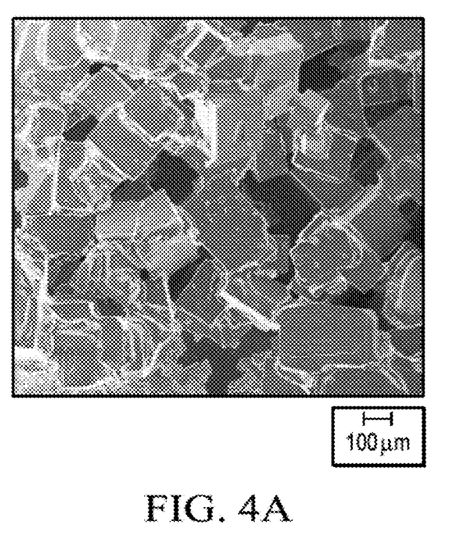
FIG. 4A-4C are scanning electron micrographs of synthesized sodium chloride crystals in accordance with an embodiment of the present disclosure.
Figure 4B:
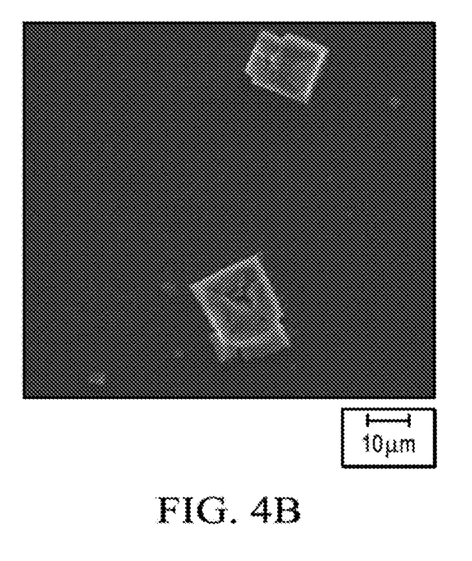
Figure 4C:
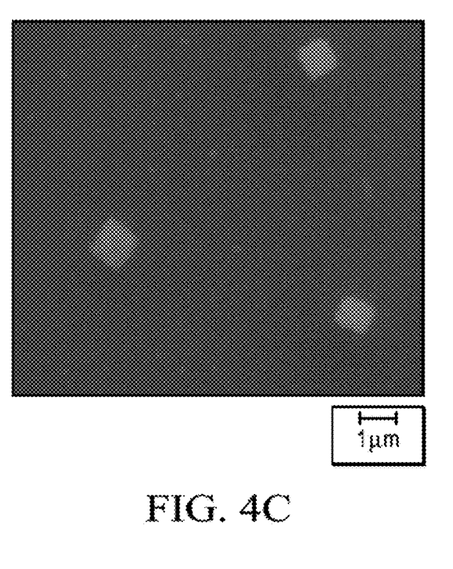

FIGS. 4A-4C are SEM images of sodium chloride (NaCl) crystals synthesized in accordance with the method of controlled crystallization from alcoholic solvent. The crystals of FIGS. 4A-4C are substantially cubic in shape and have a controlled width of about 1-300 μm. The SEM images of FIG. 4A-4C were taken by scanning electron microscopy (SEM, JEOL 7100) at 15 kV, and no additional coating was applied onto the sample surface.

In this disclosure, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed in this disclosure, and not otherwise defined, is for the purpose of description only and not of limitation. Any use of section headings is intended to aid reading of the document and is not to be interpreted as limiting; information that is relevant to a section heading may occur within or outside of that particular section.

In this disclosure, "approximately" or "substantially" means a deviation or allowance of up to 10 percent (%) and any variation from a mentioned value is within the tolerance limits of any machinery used to manufacture the part. Likewise, "about" can also allow for a degree of variability in a value or range, for example, within 10%, within 5%, or within 1% of a stated value or of a stated limit of a range.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "0.1% to about 5%" or "0.1% to 5%" should be interpreted to include about 0.1% to about 5%, as well as the individual values (for example, 1%, 2%, 3%, and 4%) and the sub-ranges (for example, 0.1% to 0.5%, 1.1% to 2.2%, 3.3% to 4.4%) within the indicated range. The statement "X to Y" has the same meaning as "about X to about Y," unless indicated otherwise. Likewise, the statement "X, Y, or Z" has the same meaning as "about X, about Y, or about Z," unless indicated otherwise.

While this disclosure contains many specific implementation details, these should not be construed as limitations on the subject matter or on what may be claimed, but rather as descriptions of features that may be specific to particular implementations. Certain features that are described in this disclosure in the context of separate implementations can also be implemented, in combination, or in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Nevertheless, it will be understood that various modifications, substitutions, and alterations may be made. While operations are depicted in the drawings or claims in a particular order, this should not be understood as requiring that such operations be performed in the particular order shown or in sequential order, or that all illustrated operations be performed (some operations may be considered optional), to achieve desirable results. Accordingly, the previously described example implementations do not define or constrain this disclosure.

What is claimed is:

1. A method comprising:
    mixing spherical grains and sacrificial particles in a suspension, wherein the sacrificial particles are larger than the spherical grains;
    injecting the suspension into a channel in a microfluidic chip, the spherical grains forming microporous structures in the channel;
    sintering the microporous structures in the channel; and
    injecting a solvent into the channel, the solvent dissolving the sacrificial particles and forming macropores between at least some of the microporous structures, thereby forming a mixed-porosity microfluidic chip.

2. The method of claim 1, further comprising using the mixed-porosity microfluidic chip to model a subsurface reservoir.

3. The method of claim 2, wherein the reservoir is a carbonate reservoir characterized by bi-modal porosity.

4. The method of claim 2, wherein modeling the subsurface reservoir comprises studying rock-fluid interactions.

5. The method of claim 2, wherein modeling the reservoir comprises spectroscopic studies of interactions between fluids and surfaces.

6. The method of claim 2, wherein modeling the subsurface reservoir comprises studying oil-water phase behavior in the pores of the mixed-porosity microfluidic chip.

7. The method of claim 1, wherein the microfluidic chip is an optically transparent or translucent chip.

8. The method of claim 1, wherein the spherical grains are calcium carbonate spheres.

9. The method of claim 8, further comprising synthesizing the calcium carbonate spheres.

10. The method of claim 1, wherein the sacrificial particles are sodium chloride crystals and the solvent is water.

11. The method of claim 1, wherein the microporous structures comprise micropores between the spherical grains, and wherein the average width of the macropores is at least about ten times larger than the average width of the micropores.

12. The method of claim 8, wherein the calcium carbonate spheres are from about 25 nanometers to about 25 microns in diameter.

13. The method of claim 10, wherein the sodium chloride crystals have a width of about 10 microns to about 250 microns.

\* \* \* \* \*